(12) United States Patent  (10) Patent No.:    US 8,052,671 B2
Christensen et al.  (45) Date of Patent:    Nov. 8, 2011

(54) INTRA-ABDOMINAL PRESSURE MONITORING DEVICE AND METHOD

(75) Inventors: Mark A. Christensen, Salt Lake City, UT (US); Timothy R. Wolfe, Salt Lake City, UT (US); Perry W. Croll, Salt Lake City, UT (US); Marshall T. Denton, Salt Lake City, UT (US); Edward J. Kimball, Salt Lake City, UT (US)

(73) Assignee: AbViser Medical, LLC, Salt Lake City, UT (US)

( * ) Notice: Subject to any disclaimer, the term of this patent is extended or adjusted under 35 U.S.C. 154(b) by 1027 days.

(21) Appl. No.: 11/665,133

(22) PCT Filed: Oct. 11, 2004

(86) PCT No.: PCT/US2004/033463
§ 371 (c)(1),
(2), (4) Date: Apr. 11, 2007

(87) PCT Pub. No.: WO2006/041496
PCT Pub. Date: Apr. 20, 2006

(65) Prior Publication Data
US 2008/0114316 A1    May 15, 2008

(51) Int. Cl.
*A61M 1/00* (2006.01)
(52) U.S. Cl. .................... 604/540; 604/93.01
(58) Field of Classification Search .......... 600/561, 600/591; 604/93.01, 540
See application file for complete search history.

(56) References Cited

U.S. PATENT DOCUMENTS
1,600,793 A    9/1926  Bogan
(Continued)

FOREIGN PATENT DOCUMENTS
DE           19530440          2/1997
(Continued)

OTHER PUBLICATIONS
PCT International Search Report, PCT/AU2004/000282, dated Apr. 28, 2004.
(Continued)

*Primary Examiner* — Melanie Hand
(74) *Attorney, Agent, or Firm* — TraskBritt, P.C.

(57) ABSTRACT

An apparatus for monitoring the intra-abdominal pressure of a patient includes a urinary catheter (102) connected to a urine valve (250) providing selectable communication between a discharge end of the urinary catheter (102) and either a drain (224) or a fluid source (104). Preferably, the urine valve (250) is adapted for remote actuation and has a housing adapted to resist patient discomfort from leg-valve (250) contact. Plumbing structure desirably maintains fluid supply (225) and drain (223) conduits in a substantially parallel arrangement to assist routing those conduits (225, 223) between a patient's legs. When the urine valve (250) is oriented to permit communication with the fluid source (104), an infusion pump (116') may be used to infuse a known quantity of fluid through the urine valve (250) and into the patient's bladder (216). A pressure transducer (218) desirably is connected in-circuit to indicate the fluid's pressure and avoid pressure fluctuations induced by system components. To facilitate the infusion process, an automatic flow control device may be included in a fluid supply path (225) and arranged to permit repetitive operation of a syringe (116') to inject a bolus of fluid into the patient's bladder (216). Subsequent to making a pressure measurement, the urine valve (250) is returned to the bladder (216) draining position.

20 Claims, 9 Drawing Sheets

U.S. PATENT DOCUMENTS

| | | | |
|---|---|---|---|
| 1,666,332 | A | 5/1927 | Hirsch |
| 1,712,848 | A | 5/1929 | Rose |
| 2,417,994 | A | 3/1947 | Sheets |
| 2,716,017 | A | 8/1955 | Linker |
| 3,100,490 | A | 8/1963 | Robert |
| 3,103,229 | A | 9/1963 | Smith |
| 3,620,255 | A | 11/1971 | Stillman |
| 3,674,052 | A | 7/1972 | Hartman et al. |
| 3,794,043 | A | 2/1974 | McGinnis |
| 4,210,173 | A | 7/1980 | Choksi et al. |
| 4,217,911 | A | 8/1980 | Layton |
| 4,301,811 | A | 11/1981 | Layton |
| 4,538,621 | A | 9/1985 | Jarczyn |
| 4,705,073 | A | 11/1987 | Beck |
| 4,966,161 | A | 10/1990 | Wallace et al. |
| 5,064,165 | A | 11/1991 | Jerman |
| 5,207,641 | A | 5/1993 | Allton |
| 5,385,563 | A | 1/1995 | Gross |
| 5,433,216 | A | 7/1995 | Sugrue et al. |
| 5,540,668 | A | 7/1996 | Wilson et al. |
| 5,647,845 | A | 7/1997 | Haber et al. |
| 5,713,850 | A | 2/1998 | Heilmann et al. |
| 5,865,764 | A | 2/1999 | Moorhead |
| 5,899,434 | A | 5/1999 | Nishimura |
| 5,916,153 | A | 6/1999 | Rhea |
| 5,916,230 | A | 6/1999 | Brenneman et al. |
| 6,102,888 | A | 8/2000 | Walker |
| 6,287,265 | B1 | 9/2001 | Gleason |
| 6,334,064 | B1 | 12/2001 | Fiddian-Green |
| 6,382,001 | B1 | 5/2002 | Neeley et al. |
| 6,434,418 | B1 | 8/2002 | Neal et al. |
| 6,447,462 | B1 | 9/2002 | Wallace et al. |
| 6,494,208 | B1 | 12/2002 | Morejon |
| 6,503,208 | B1 | 1/2003 | Skovlund |
| 6,602,243 | B2 | 8/2003 | Noda |
| 6,645,183 | B2 | 11/2003 | Christensen |
| 6,877,714 | B2 | 4/2005 | Hall |
| 7,097,632 | B2 | 8/2006 | Shia et al. |
| 7,112,177 | B2 | 9/2006 | Christensen et al. |
| 7,240,740 | B2 | 7/2007 | Reilly et al. |
| 7,381,190 | B2 | 6/2008 | Sugrue et al. |
| 7,389,947 | B2 | 6/2008 | Denton |
| 7,644,722 | B2 | 1/2010 | Christensen |
| 7,726,328 | B2 | 6/2010 | Christensen et al. |
| 2002/0065472 | A1 | 5/2002 | Brockway et al. |
| 2002/0082610 | A1 | 6/2002 | Cioanta et al. |
| 2002/0115966 | A1 | 8/2002 | Christensen et al. |
| 2003/0062281 | A1 | 4/2003 | Giard et al. |
| 2003/0195478 | A1 | 10/2003 | Russo |
| 2004/0082909 | A1 | 4/2004 | Shia et al. |
| 2004/0176703 | A1* | 9/2004 | Christensen et al. ......... 600/561 |
| 2005/0131357 | A1 | 6/2005 | Denton et al. |
| 2006/0058702 | A1 | 3/2006 | Christensen et al. |
| 2006/0079804 | A1 | 4/2006 | Sugrue et al. |
| 2006/0178571 | A1 | 8/2006 | Barnett |
| 2007/0255167 | A1 | 11/2007 | Christensen et al. |
| 2008/0103408 | A1 | 5/2008 | Denton et al. |
| 2008/0114316 | A1 | 5/2008 | Christensen et al. |

FOREIGN PATENT DOCUMENTS

| | | |
|---|---|---|
| EP | 0 258 690 | 8/1987 |
| GB | 2123300 A | 2/1984 |
| JP | 9-72252 | 3/1997 |
| JP | 10-305104 | 11/1998 |
| JP | 11-503926 | 4/1999 |
| JP | 11-155821 | 6/1999 |
| JP | 11-263587 | 9/1999 |
| JP | 2002-360705 | 12/2002 |
| WO | WO 96/22118 | 7/1996 |
| WO | WO 98/42397 | 10/1998 |
| WO | WO 2004/078235 | 9/2004 |
| WO | WO 2004/078235 A2 | 9/2004 |
| WO | WO 2004/080519 A1 | 9/2004 |
| WO | WO 2006/060248 | 2/2007 |

OTHER PUBLICATIONS

PCT Written Opinion, PCT/AU2004/000282, dated Apr. 28, 2004.
PCT International Search Report and Written Opinion, PCT/US04/06409, dated Dec. 26, 2006.
Fusco et al., "Estimation of Intra-abdominal Pressure by Bladder Pressure Measurement: Validity and Methodology," The Journal of Trauma® Injury, Infection and Critical Care, Feb. 2001, pp. 297-302, vol. 50, No. 2.
Kirkpatrick et al., "Is Clinical Examination an Accurate Indicator of Raised Intra-abdominal Pressure in Critically Injured Patients?" CJS, Jun. 2000, pp. 207-211, vol. 43, No. 3.
Lozen et al., "Intraabdominal Hypertension and Abdominal Compartment Syndrome in Trauma: Pathophysiology and Interventions," AACN Clinical Issues: Advanced Practice in Actue Critical Care, Feb. 1999, pp. 104-112, vol. 10, No. 1.
Malbrain et al., "Abdominal pressure in the critically ill: measurement and clinical relevance," Intensive Care Med, 1999, pp. 1453-1458, vol. 25.
Sugrue et al., "Intra-abdominal pressure: time for clinical practice guidelines?" Intensive Care Med, 2002, pp. 389-391, vol. 28.
International Preliminary Report on Patentability, PCT/US2004/033463, dated Apr. 11, 2007.
Partial European Search Report for EP 04 79 4734 dated May 29, 2009.
U.S. Appl. No. 11/825,215, filed Jul. 3, 2007, Apparatus for Monitoring Intra-Abdominal Pressure.
U.S. Appl. No. 60/971,820, filed Sep. 12, 2007, Applicator for Oro-Pharyngeal Anesthetic.
PCT Search Report and Written Opinion, PCT/US2005/042406, dated Sep. 18, 2006.
PCT International Preliminary Report on Patentability, PCT/US2005/042406, dated Jun. 5, 2007.
Cheatham et al., Intra-abdominal Pressure: A Revised Method for Measurement, 1997, pp. 594-595, Elsevier Science Inc.
Burch et al., Abstract, The abdominal compartment syndrome, Surg. Clin. North Am., 1996, pp. 833-842, vol. 76.
Kron et al., The measurement of intra-abdominal pressure as a criterion for abdominal re-exploration, Ann. Surg., 1984, pp. 28-30, vol. 199.
Iberti et al., Abstract, A simple technique to accurately determine intra-abdominal pressure, Crit. Care Med., 1987, pp. 1140-1142, vol. 15.
Iberti et al., Abstract, Determination of intra-abdominal pressure using a transurethral bladder catheter: clinical validation of the technique, Anesthesiology, 1989, pp. 47-50, vol. 70.
Platt et al., Abstract, Mortality associated with nosocomial urinary-tract infection, N. Eng. J. Med., 1982, pp. 637-642, vol. 307.
Office Action for U.S. Appl. No. 11/219,319, dated Feb. 6, 2009.
Office Action for U.S. Appl. No. 11/219,319, dated Jul. 10, 2009.
Office Action for U.S. Appl. No. 11/219,319, dated May 14, 2008.
Office Action for U.S. Appl. No. 11/219,319, dated Mar. 31, 2010.
Office Action for U.S. Appl. No. 11/825,215, dated Dec. 16, 2008.
Office Action for U.S. Appl. No. 11/825,215, dated Sep. 28, 2009.
Supplementary Partial European Search Report for EP 04 79 4734 dated May 29, 2009.

* cited by examiner

INTRA-ABDOMINAL PRESSURE MONITORING DEVICE AND METHOD

TECHNICAL FIELD

The invention relates generally to medical devices, particularly to apparatus configured as an assembly to infer intra-abdominal pressure of a medical patient by measuring bladder pressure.

BACKGROUND

Elevated intra-abdominal pressure leads to major changes in the body's physiology that, if undetected and untreated, can result in organ damage and patient death. When patients become critically ill, they may develop a capillary leak phenomenon that causes the tissues in their body to become edematous with extra fluid that seeps out of the capillaries. This process is called "3rd spacing" of fluid. It is very common in sepsis, burn, trauma, and post-operative patients. One area of the body where 3rd spacing is especially prevalent is the abdominal cavity. Critically ill patients can have many liters of fluid leak into the intestinal wall, the intestinal mesentery, and the abdominal cavity (as free fluid sloshing around the intestines).

Fluid 3rd spacing in the abdominal cavity results in an increase in intra-abdominal pressure (IAP). Normal IAP is 0 mm Hg to subatmospheric (less than 0). Once the pressure builds to 12-15 mm Hg, intra-abdominal hypertension (IAH) occurs. At this point, methods to improve intestinal perfusion should be started, such as: fluid loading to increase blood flow to gut, inotropic support to increase cardiac output, etc. As pressures increase above 20-25 mm Hg, the abdominal compartment syndrome (ACS) exists and major physiologic and organ system dysfunction result. Decompressive surgery (vertical midline abdominal incision) is often required to prevent irreversible organ damage and death. The exact pressure at which abdominal decompression should occur is dependent on a number of host factors including age, underlying co-morbidities and physiologic evidence of developing ACS.

Early detection of increasing abdominal pressure allows the clinician to intervene before irreversible organ damage occurs and may be life saving. The only reliable method for early detection of increasing IAP is to place a catheter within a space in the abdomen (e.g., peritoneal cavity, stomach, bladder, rectum) and measure the pressure. The most commonly used method is to monitor bladder pressure through an indwelling Foley catheter. To monitor bladder pressure, clinicians are currently building their own devices out of many separate materials and inserting them into the Foley catheter.

Currently employed techniques used to monitor a patient's IAP are adapted to measure the pressure of fluid contained within the patient's bladder at intervals spaced apart in time. While the pressure reading at a pressure transducer may not correspond to the actual value of IAP (e.g., if the transducer is located at a different elevation than the bladder), trends in measured pressure will correlate to trends in IAP in the patient.

One way to measure a patient's IAP involves disassembling a urinary catheter drain tube to inject saline through the catheter and into the patient's bladder. (For convenience, a urinary catheter will generally be referred to in this disclosure as a Foley catheter, due to its common use). Unfortunately, opening the closed drainage system plumbing places both the patient and the health practitioner at increased risk of infection. It is possible to use a three-way Foley catheter, but such catheters are more expensive and are not routinely used. Use of a three-way Foley catheter would require either preknowledge of its necessity, or replacement of a standard catheter. The former option increases costs, and the latter would increase both costs and risk of patient infection.

A different approach for introducing a bolus of fluid into a patient's bladder incorporates the aspiration port included in a urinary catheter drain system as a fluid injection port. The drain tube connected to the Foley catheter is blocked, and the needle of a syringe is passed through the drain tube's aspiration port to permit injection of a saline bolus. A manometer or pressure transducer is then connected to the needle to record bladder pressure. Undesirably, approaches involving use of needles, particularly in the vicinity of the patient's legs to assemble the pressure measuring apparatus, place both the patient and the health practitioner at risk of needle sticks.

With reference to FIG. 1, a currently used arrangement adapted to monitor a medical patient's IAP is generally indicated at 100. A patient is fitted with a urinary catheter 102, such as a Foley catheter. A fluid source, such as saline bag 104, is connected in fluid communication to the catheter 102 upstream of an occluding device 108 temporarily applied to block the catheter drain conduit 106. Interruption of the urine drain path from the patient generally is permitted only temporarily as required to effect pressure measurements.

The device 100 includes a pair of two-way or three-way stopcocks, 110 and 112, respectively. One end of fluid supply tube 114 is connected to a one liter saline bag 104. The other end of fluid supply tube 114 is connected to an inlet port of stopcock 110. A valve stem in stopcock 110 may be oriented to permit fluid to flow from bag 104 toward syringe 116. When syringe 116 is full, or charged with fluid as desired, the valve stem of stopcock 110 is adjusted by way of a manual rotation to permit fluid flow from the syringe toward stopcock 112 while resisting fluid flow toward bag 104. Stopcock 112 can be adjusted to direct a bolus of fluid from syringe 116 for flow through tubing 120 towards catheter 102. Stopcock 112 may also be adjusted to an alternate configuration to provide fluid communication between a pressure measuring device 121 and tubing section 120 while resisting fluid flow toward stopcock 110. An infusion needle or angiocatheter 122 carried at an end of tubing 120 is inserted into urine collection port 125 to couple the tube 120 in fluid communication to the catheter 102.

The steps typically required to measure a patient's IAP, using the arrangement of FIG. 1, are as follows: First the apparatus 100 is assembled, including inserting the needle of an angiocatheter 122 into aspiration port 125 connected to a Foley catheter 102 installed in a patient. Stopcock 110 is oriented to permit fluid flow between bag 104 and syringe 116, and the syringe is filled with saline. Stopcocks 110 and 112 are then both adjusted for fluid flow from the syringe 116 toward the catheter 102. Tube 120 is flushed and filled with saline. Then tubing 106 is occluded to resist fluid flow in a drain direction from catheter 102. Typically, stopcock 112 is then adjusted to resist fluid flow toward syringe 116 and stopcock 110 is configured to permit fluid flow between bag 104 and syringe 116 so that the syringe 116 can be refilled with saline. After priming syringe 116, stopcock 110 and 112 are adjusted for fluid flow between syringe 116 and catheter 102 to place a bolus of fluid into the patient's bladder. Then, stopcock 112 is oriented to provide fluid communication between conduit 120 and pressure transducer 121 while resisting fluid flow toward stopcock 110. Pressure apparatus 121 then indicates the current pressure in the patient's bladder, which may be correlated to IAP. Subsequent to making and recording the pressure measurement, the occlusion of drain 106 is removed to permit draining the bolus of fluid from the patient's bladder. Such procedure is repeated at intervals spaced apart in time to record trends in the patient's IAP. The bolus of injected fluid desirably is less than about 100 mL and of uniform size during each successive pressure measurement to avoid effect from bladder wall musculature on measured pressure.

Occluding device 108 may be a clamp or hemostat as illustrated, or sometimes may be a valve. However, operable medical grade valves that are commercially available, such as two-way or three-way stopcocks 110 and 112, typically introduce undesired complications. One complication is that the available medical grade stopcocks typically provide drainage passageways that are too small in diameter for use in a urinary catheter drain. Clogging of the urine drain bore would be a serious problem.

The most desirable location of a catheter drain-occluding valve (urine valve) for an IAP measurement system is in close proximity to the catheter 102—therefore between the patient's legs. Another complication substantially precluding direct inclusion of commercially available medical grade two-way or three-way valves or stopcocks is that such devices route fluid conduits in orthogonal directions at the valve connection locations, thereby creating protruding and invasive plumbing that is uncomfortable to the patient. Furthermore, currently available valves and stopcocks also have protrusions (such as valve actuators or handles), and sharp corners or abrupt changes in shape, that place a patient at risk of injury should such protrusion or corner be impressed into a patient's skin.

Because the most desirable plumbing arrangement places the urine valve between a patient's legs, manual actuation of that valve requires a health practitioner to gain physical access to the groin area of a patient. In a surgical setting, the anesthesiologist is the most likely party to assume responsibility for monitoring the patient's IAP. Traditionally, the anesthesiologist is stationed at the patient's head for convenient administration of anesthesia and monitoring of the patient's condition. All monitoring apparatus required by the anesthesiologist desirably is located in close proximity, or in a line-of-sight, to reduce moving about of personnel in the operatory theater.

Historically, in surgeries not involving the head of a patient, the patient's head area is regarded as the "turf" of the anesthesiologist. Correspondingly, the rest of the patient's body is regarded as the "turf" of the surgeon. It is undesirable for the anesthesiologist to move from a traditional station, at the patient's head, repeatedly to make periodic IAP measurements. Further, it would be impolitical to require an anesthesiologist to invade the "turf" of the surgeon to effect the IAP measurement. In any case, periodic manual activation of a urine valve by the anesthesiologist, or other personnel present in the operatory, also may cause an interference with the surgeon.

The procedures for measuring trends in a patient's IAP described above undesirably place a patient at risk of infection, or require tiresome manual adjusting of a plurality of plumbing devices, such as two-way valves or stopcocks. It would be a desirable improvement to provide a device for measuring trends in a patient's IAP that is faster and more simple to operate. It would be a further advance to eliminate operations requiring needles to assemble or use the pressure measurement apparatus. A still further advance in the art would enhance the patient's comfort and increase the patient's protection from injury by resisting contact between the patient and uncomfortable or even harmful medical apparatus. A still further advance would provide for actuation of the urine drain valve from a location remote from that valve.

DISCLOSURE OF INVENTION

An apparatus and method for measuring hydraulic pressure in the bladder of a medical patient to infer intra-abdominal pressure (IAP). The IAP measurement procedure can be performed manually, or with an automated system. Certain embodiments of the invention can incorporate automated fluid pumping and valve actuation operable to record IAP at programmed intervals of time without requiring human intervention. Pressure measurements can be displayed at local and/or remote locations. Therefore, a health practitioner can remain at a remote central location and monitor the vital statistics, including IAP, of a plurality of patients.

One operable assembly for inferring a patient's IAP includes: a catheter adapted for draining urine from the patient's bladder, a container of fluid, an infusion pump, a pressure transducer, and a urine valve. The urine valve is connected to a drain portion of the catheter, and may be placed into a drain configuration or an infusion configuration. The drain configuration permits draining of fluid from the bladder. The infusion configuration resists such draining, and permits infusion of fluid into the bladder. The pump is placed in-circuit between the urine valve and the container of fluid, and is operable to infuse fluid from the container into the bladder. The pressure transducer is placed in-circuit and desirably isolated from pressure fluctuations associated with the pump. Such arrangement is effective for the transducer to generate a signal responsive substantially to true gage pressure of infused fluid in the bladder. Desirably, the transducer also is isolated from a head pressure that may be associated with fluid in the container.

A urine valve may be actuated by direct manual manipulation, or by an input generated at a remote location. In certain currently preferred embodiments of a urine valve, the valve is remotely actuatable to change a configuration of the valve from drain to infusion. In any case, a urine valve may be actuated from an infusion configuration to a drain configuration manually, autonomically, or by remote actuation.

One operable type of remotely actuatable urine valve is operated hydraulically by a fluid input received from the pump. A gate component of the hydraulic urine valve is displaced by flow of fluid that has been pressurized by the pump to place the valve into the infuse configuration. A gate component may be arranged for rotary or reciprocal motion with respect to a valve housing. In certain hydraulic valves operable in embodiments of the invention, a gate component is also displaced by a hydraulic input received from the pump effective to place the valve into drain configuration.

Some embodiments of operable urine valves include a biasing member arranged to urge the gate toward a drain configuration. Such biasing member can include a resilient element disposed for biasing by action of a hydraulic input, manual input, or electro-mechanical input. Sometimes, a time-delay mechanism is included in a urine valve to permit substantially autonomic opening of the valve, to return the valve to a drain configuration.

A currently preferred type of hydraulic urine valve includes a housing defining a chamber having a volume, with an infusion port and a drain exit port being in fluid communication with the chamber. The valve gate includes a piston having a portion disposed to reciprocate between first and second positions in the chamber and operable to divide the chamber into at least a first subchamber and a second subchamber. The infusion port is arranged in fluid communication with the first subchamber. The drain exit port is arranged in fluid communication with the second subchamber. Structure associated with the piston provides a drain entrance port and a bypass port. When the piston is at the first position, the valve is configured to permit fluid communication between the drain entrance port and the drain exit port while resisting fluid communication between the drain entrance port and the infusion port. When the piston is at the second position, the valve is configured to permit fluid communication between the drain entrance port and the infusion port by way of the bypass port while resisting fluid communication between the drain entrance port and the drain exit port. Desirably, the piston is biased toward the first position such that the bypass port is occluded by structure associated with the housing substantially upon cessation of fluid flow through the infusion port and into the first subchamber.

Certain preferred urine valves include a time-delay mechanism adapted to permit substantially autonomic opening of the valve to effect a draining discharge. One operable time-delay mechanism includes a bleed-down port having a cross-section sized to provide restricted fluid flow therethrough between the first subchamber and the second subchamber, and a resilient member biased to urge the piston toward the second configuration.

One currently preferred method for measuring hydraulic pressure in the bladder of a medical patient to infer intra-abdominal pressure in that patient, includes: a) providing a catheter adapted for draining urine from the bladder, a container of infusion fluid, a pump, a pressure transducer; and a urine valve; b) placing the urine valve in-circuit between a drain portion of the catheter and a receptacle; c) placing said pump in-circuit between the urine valve and container; d) placing the pressure transducer in-circuit with the catheter effective to isolate the pressure transducer from pressure fluctuations associated with actuation of the valve; e) bleeding air from the circuit; f) placing the urine valve into a draining configuration, for a first period of time, to permit flow between the catheter and receptacle while resisting flow between the container and catheter; g) placing the urine valve into an infusion configuration, for a second period of time, to resist flow between the catheter and receptacle while permitting flow between the container and catheter; h) infusing a desired bolus of infusion fluid into the bladder during the second period of time; i) measuring a pressure in the bladder at least once during a third period of time while the urine valve is in a pressure-reading configuration; and j) returning the urine valve to a draining configuration subsequent to lapse of the third period of time.

Sometimes, step d) further includes, in any order: applying a first pressure, above atmospheric pressure, to the infusion fluid; and placing the pressure transducer in-circuit effective substantially to isolate it from the first pressure. Step g) may include operating the pump for a portion of the second period of time to cause a gate member of the urine valve to displace operably to place the urine valve into the infusion configuration. Step j) may include operating the pump to cause a gate member of the urine valve to displace and return the urine valve to the draining configuration. In some instances, a gate member of the urine valve is configured and arranged in harmony with a time-delay mechanism effective to maintain the urine valve in the pressure-measuring configuration during the third period of time and then is effective autonomically to return the urine valve to the draining configuration. It is generally desirable, prior to step e), to apply a pressure above atmospheric pressure to the infusion fluid. In such case, step e) typically includes actuating a flow restriction device disposed in-circuit between the container and the pressure transducer operably to permit an increased flow rate through the flow restriction device.

BRIEF DESCRIPTION OF DRAWINGS

In the drawings, which illustrate what are currently considered to be the best modes for carrying out the invention.

BEST MODE FOR CARRYING OUT THE INVENTION

Figure 2:
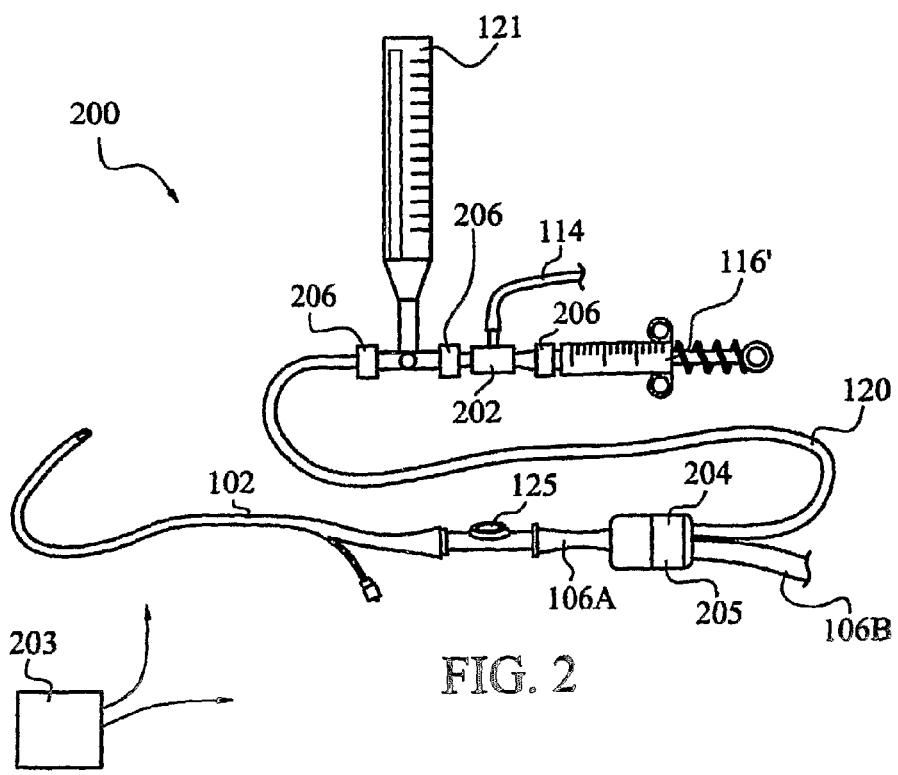
FIG. 2 is a schematic plan view illustrating a first assembly for measuring a patient's bladder pressure according to principles of the invention.

FIG. 2 illustrates one currently preferred embodiment, generally indicated at 200, of an apparatus for measuring trends in a patient's intra-abdominal pressure. The assembly 200 includes a fluid supply conduit 114 with one end in fluid communication with a sterile saline or other fluid source (not illustrated). Conduit 114 desirably is connected at a second end for fluid communication with an automatic, direction-of-flow control device 202 to urge fluid flow through conduit 120 in a direction toward a patient. A hydraulic pressure in conduit 120 is measured by a pressure transducer, such as transducer 121.

Figure 1:
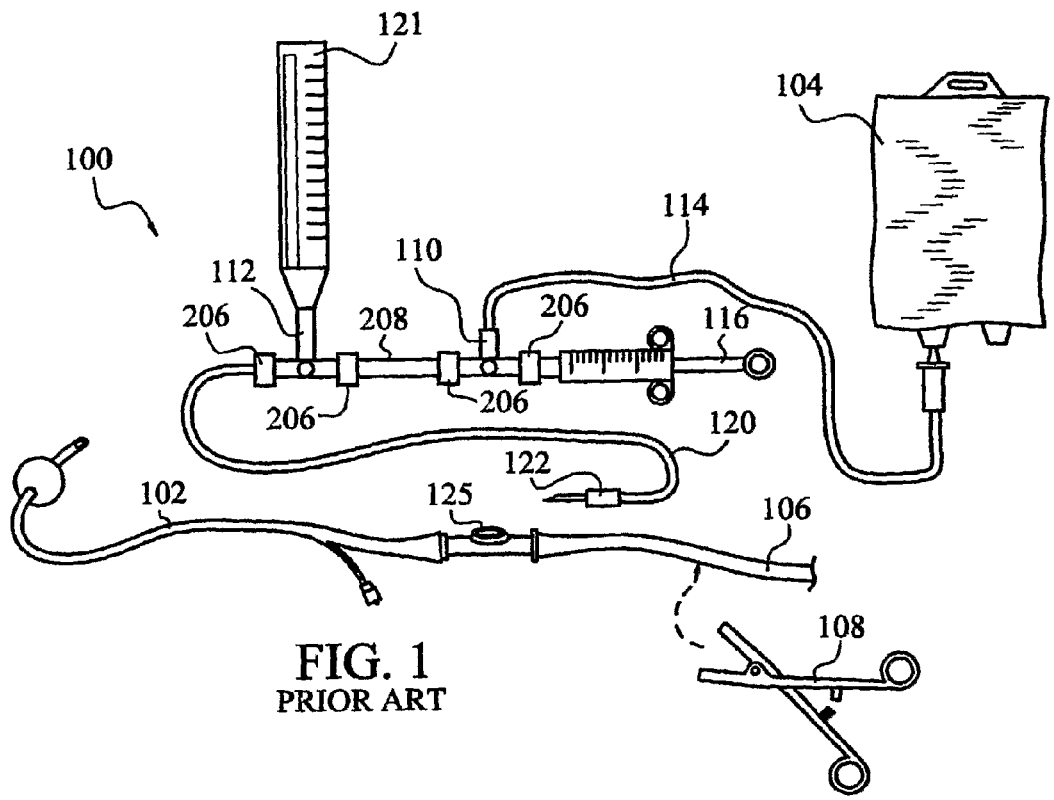
FIG. 1 is a schematic plan view illustrating a prior art assembly operable to measure a patient's bladder pressure.
Figure 3:
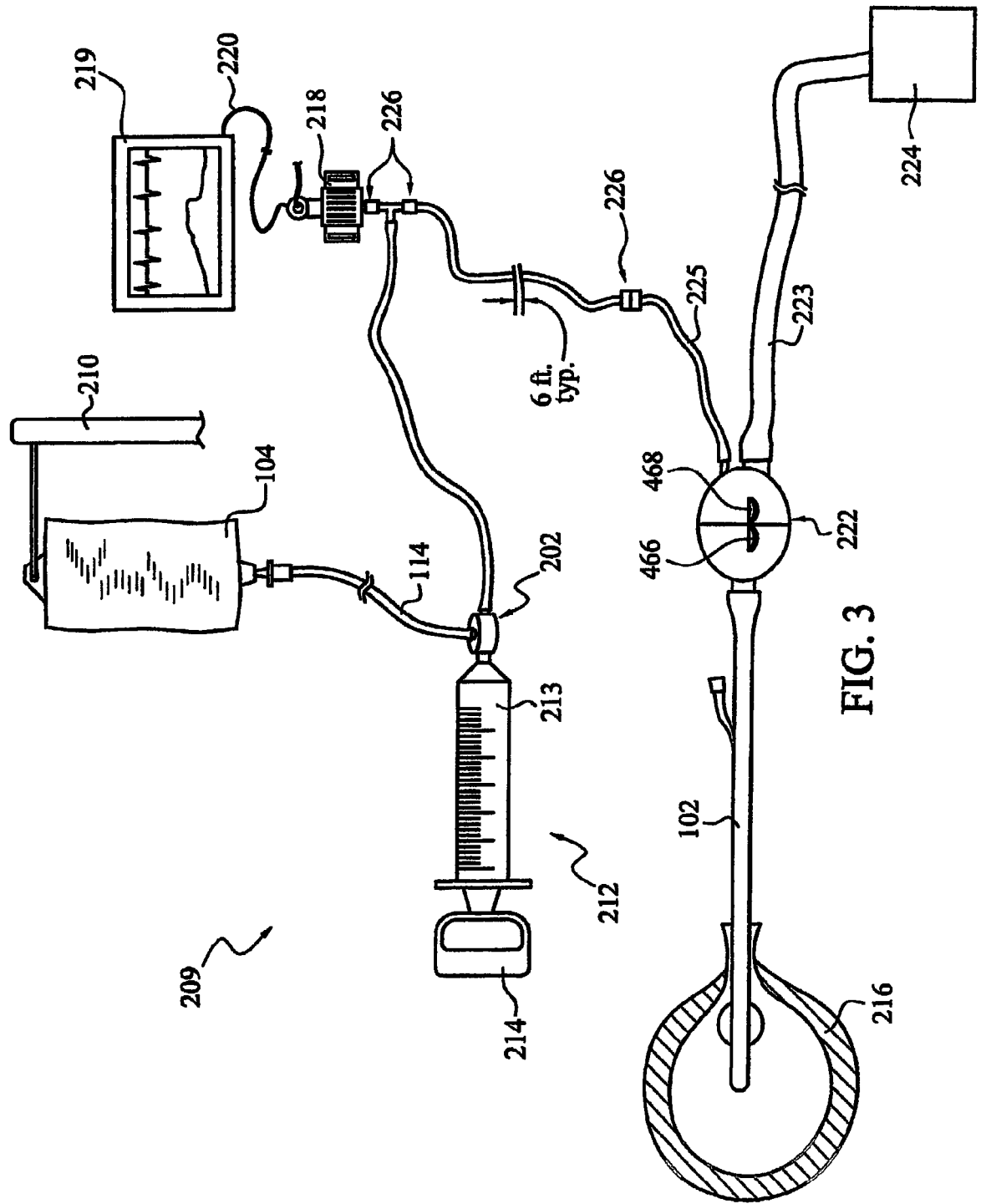
FIG. 3 is a schematic plan view illustrating a second arrangement of equipment for measuring a patient's bladder pressure according to principles of the invention, which locates a pressure transducer remote from the patient.

As illustrated in FIG. 3, it is sometimes preferred to arrange the pressure transducer in a dead-ended conduit, compared to the flow-through arrangements illustrated in FIGS. 1 and 2. The preferred arrangement requires a clinician to make only one attachment at the pressure transducer area. It should be realized that additional components, such as zeroing stopcocks, may be included in desired plumbing arrangements and may not be illustrated in certain of the FIGs. for various reasons. For example, and with reference still to FIG. 3, such a zeroing stopcock often is placed into position at a joint 226 between the 'T' connector and the pressure transducer 218. Such a stopcock may be installed for convenience in purging air from the system, to facilitate maintaining a sterile field inside conduit 225, and/or to isolate the pressure transducer from the conduit system for purpose of establishing a baseline pressure, or zero, for an output of the transducer 218.

With reference again to FIG. 2, one preferred embodiment of the invention is provided as a substantially preassembled kit-in-a-package 203. A preferred embodiment of the kit 203 reduces chance of error by simplifying assembly of an IAP apparatus and reducing the number of decisions a clinician must make. Such a kit requires a clinician only to make a first connection to a saline bag 104, a second connection to a pressure transducer, and a third connection between an indwelling catheter and a urine drain container. Package 203 desirably is made from a material operable to maintain sterility of the assembled components included in the kit as the kit is transported and stored prior to use.

Flow control device 202 can generally be characterized as being cyclically operable with a staging infusion pump, such as a syringe, to permit fluid flow from a fluid source during a filling stroke of the staging pump, and to resist fluid flow towards the fluid source during an expelling stroke of the staging pump. Typically, one or more seal members carried inside of device 202 is/are biased for automatic operation to control a direction of fluid flow through the device 202. Therefore, a health practitioner is relieved of the tedious chore of adjusting the valve 202 manually to control a direction of fluid flow between cycles of an infusion pump such as a syringe. Devices within contemplation for use as a flow control device 202 include a pair or more of check valves, a double check valve, a check-bypass valve, and a check/restricted flow-bypass valve. Flow control device 202 may sometimes be embodied by a single multifunction component, or may include an assembly of single—and/or multifunction devices.

As illustrated in FIG. 2, assembly 200 includes a remotely actuatable valve 204 connected in fluid communication with a discharge port from flow control device 202. Valve 204 may sometimes also be referred to in this disclosure as a type of urine valve, or a urine discharge or drain valve. Valve 204 desirably is located in close proximity to a discharge of a Foley catheter 102 installed in a patient. A Foley catheter is not required, per se—virtually any sort of urine draining catheter may be used. An operable catheter is commercially available from CR Bard, Inc. of New Jersey, under part No. 265716.

As illustrated in FIG. 2, valve 204 can be connected in fluid communication to Foley catheter 102 by way of a relatively short section of urine drain conduit 106A. Such close proximity to a discharge of catheter 102 reduces a volume of fluid required to be pumped through the system to effect a pressure measurement, and also helps to maintain the apparatus 200 in a tidy, organized arrangement. Inclusion of a remotely actuatable valve, such as valve 204, to selectively block a discharge from the catheter 102 simplifies operation of the assembly 200 compared to the prior art, and constitutes an improvement providing several advantages.

Of course, a urine valve, such as illustrated valve 204, may be adapted to connect directly to the discharge end of a urinary catheter without an intervening conduit section 106A. It is within contemplation for a valve 204 to carry structure adapted for connection directly to structure provided at a discharge area of a catheter. In general, connections between the various components forming an assembly 200 may be made as a matter of convenience, and using any operable type of plumbing connection joint.

In the embodiment illustrated in FIG. 2, valve 202 is connected to a discharge end of spring-assisted syringe 116' through a Luer-locking type of joint 206. An alternative connection between any of the components in an IAP measuring assembly according to the invention, such as assembly 200, may include any operable fluid-tight connection formable between the components.

Stretches between components may also include intermediate structure, such as one or more sections of tubing 208 (see FIG. 1). Furthermore, the invention, such as illustrated in FIG. 2 as assembly 200, desirably is configured for arrangement of its various components in convenient and/or desirable locations. For example, bag 104 typically is suspended from an elevated hanger, but pressure indicating manometer 121, or in alternative embodiments, a pressure measuring transducer portion, desirably is located at approximately the same elevation as the patient's bladder to reflect an equivalent pressure. Intermediate tubing members (e.g., 114, 120, 208, etc.) may be provided having lengths sized to permit a desired spacing between components.

With reference still to FIG. 2, preferred embodiments of a remotely actuatable valve 204 provide connections for fluid supply conduit 120 and urine drain conduit 106B to place such conduits approximately in parallel. A substantially parallel arrangement of conduits 120 and 106B near the valve 204 can increase patient comfort and also help to maintain a tidy arrangement of assembly 200. Furthermore, the illustrated substantially in-line arrangement between conduits 106A and conduits 120 and 106B aides in routing the conduits in a path to minimize their intrusiveness to a patient.

Fluid carrying conduits may be affixed or connected to structure associated with one or more components when assembling an apparatus 200. It is currently preferred to include a short length, or pigtail, of infusion fluid supply conduit 120 permanently affixed to valve 204 when manufacturing the valve. Fluid supply conduits typically are of relatively small diameter (e.g., about 1/16 to 1/8 inches, or 1½ to 3 mm, in inside diameter) to minimize priming volume. Such a pigtail conduit typically is solvent welded, or otherwise bonded to structure associated with valve 204.

The urine drain lumen downstream of the catheter, and passing through the urine valve, desirably is of relatively larger diameter (e.g., about 3/16 to ½ inch, or 4.8 to 13 mm, in inside diameter) to resist occlusion during extended periods of use. A discharge end of a catheter 102, or tube section 106A (see FIG. 2), may be stretch-fit, to make a connection in the field, over an exterior surface of a barb-type fitting associated with valve 204. In some cases, an additional external clamp may further be applied over the catheter 102 or conduit 106A to augment the formed joint, and to resist decoupling the patient connection from the valve 204 as a bolus of fluid is injected into a patient's bladder. Similarly, a discharge conduit 106B may be attached to urine valve 204 in a plug-together fit.

Certain preferred embodiments of a urine control valve 204 may include a valve body or housing 205 shaped to provide a comfortable interface for adjacent surfaces of a patient's skin to resist contact-induced patient discomfort. One such comfort-enhancing shape includes blunt edges and rounded corners. Certain valve actuation structure of a comfort-designed urine valve 204 desirably is disposed internal to valve housing 205 to avoid protruding elements that might poke and irritate a patient.

FIG. 3 illustrates an arrangement of equipment, generally indicated at 209, for measuring IAP in a patient that locates most of the equipment at a convenient location remote from the patient. While equipment can be located at any convenient distance from the patient, it is generally located within a radius of about six to ten feet, or so. In a surgery setting, apparatus to control making and observing an IAP measurement desirably is positioned for convenient access to an anesthesiologist. The IAP measurement equipment desirably is assembled using a procedure operable to resist degrading sterility of the catheter draining system.

As indicated in FIG. 3, apparatus including the saline fluid source 104 can be suspended from equipment stands, such as stand 210. Fluid flow control device 202 and a cyclic pressure-inducing device, such as syringe 212, may be located in convenient proximity to the saline bag 104, or at some other desirable location. Illustrated syringe 212 is representative of a larger model, perhaps having a volume capacity of 50 ccs. Such a syringe 212 typically is operated using both hands. An operator grasps the syringe barrel 213 with one hand and actuates the plunger held in the other hand at transverse handle 214. In preferred embodiments of the invention, cyclic actuation of the syringe 212 automatically operates the fluid flow control device 202 to urge fluid flow in the direction toward the patient's bladder 216.

Pressure transducer 218 desirably is suspended from some structure at an elevation substantially in correspondence with the patient's bladder. Two operable pressure transducers 218, commercially known as Truwave disposable pressure transducers, are commercially available from Edwards Lifesciences under part numbers PX601 and PX600F. Transducer 218 can be affixed to a wall, stand 210, a side of the patient's bed, the patient's leg, or any other convenient location. Pressure display terminal 219 can be located as desired for convenient monitoring by a health practitioner. An electric cable 220, or wireless transmission (not illustrated) communicates the pressure signal from the transducer 218 to the display device 219.

Desirably, a large portion of an IAP measuring apparatus is provided in a preassembled form, e.g., as a kit, to reduce decision making required of clinicians. One exemplary such kit 203 (FIG. 2) simply requires spike connection of a kit's fluid supply conduit to a fluid source, such as a saline bag; connection of a pressure transducer to the kit's measurement conduit; and connection of the kit's urine valve between an indwelling catheter and drain container.

The urine discharge valve illustrated in FIG. 3, and generally indicated at 222, is adapted for hydraulic actuation, from a location remote from the valve 222, between a draining and a blocking configuration. Valve 222 is normally disposed in a draining configuration to permit discharge of urine, or other fluid, through urine catheter 102 placed into fluid communication with the patient's bladder 216. Valve 222 is normally placed into such drain configuration so that fluid drains from bladder 216, through valve 222, through drain conduit 223, and into urine collection facilities, such as bag 224.

Some urine valves 222 may include one or more sections of conduit, such as drain conduit 223 and/or fluid supply conduit 225 permanently affixed by known manufacturing methods to structure associated with the body of the valve 222. In such case, a connector, such as the luer-locking type connector generally indicated at 226, may be provided to facilitate making plumbing connections in the intra-abdominal pressure monitoring apparatus assembly.

Figure 4:
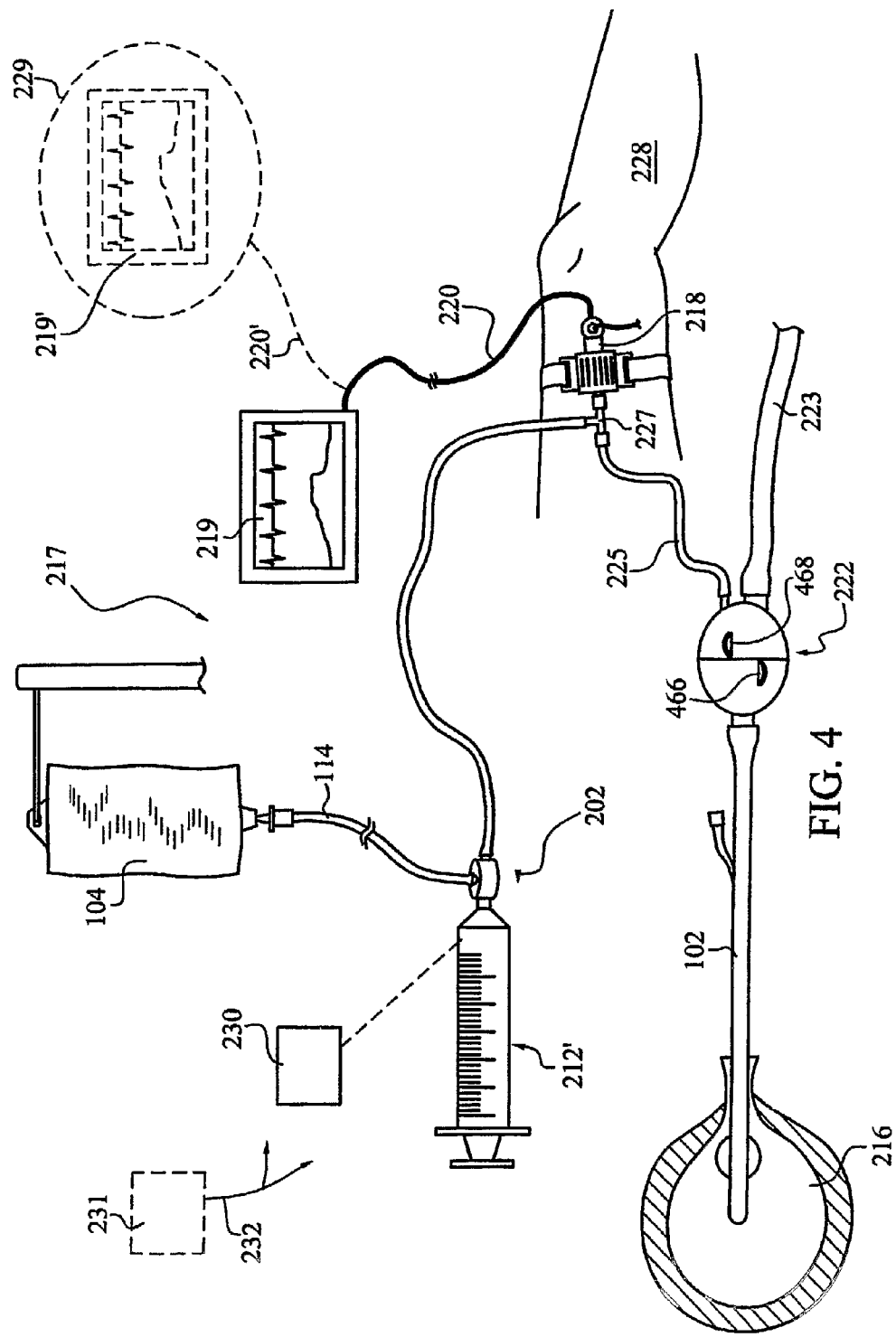
FIG. 4 is a schematic plan view illustrating a third arrangement of equipment for measuring a patient's bladder pressure according to principles of the invention, which locates a pressure transducer on the patient's leg.

The assembly to measure trends in IAP illustrated in FIG. 4, generally indicated at 217, locates the pressure transducer 218 on the patient's leg 228. A cyclic pressure-inducing device, such as the finger-actuated syringe generally indicated at 212', is illustrated in combination with a flow control device 202 for use of the thus-formed assembly as a fluid infusion pump.

Illustrated valve 222 may also be characterized as providing a streamlined plumbing arrangement, in that conduits 225 and 223 are maintained in approximately parallel alignment in the vicinity of the valve 222. In contrast to an orthogonal plumbing arrangement provided by certain prior art valves, such a streamlined plumbing configuration facilitates routing of the conduits to reduce irritation to a patient. The streamlined plumbing arrangement provided by valve 222 urges conduits 225 and 223 to follow a path between the patient's legs where the conduits are most out-of-the-way, and less likely to impact negatively on patient comfort.

In the context of the instant invention, a terminal 219 encompasses any display device operable to show a representation of data for visual acquisition by a human observer. Representative terminals 219 include CRT's, LCD panels, LED arrangements, columns of mercury or other indicating fluids, and other devices capable of producing a visible display of a representation of data, such as numbers, line plots, or bar graphs, and the like.

More than one terminal 219 may be provided, with one typically being located near the patient's bed. In a surgical theater, one such terminal desirably is placed in a line-of-sight to the anesthesiologist. As illustrated in FIG. 4, one or more terminals 219' may be disposed at one or more locations 229 remote from the patient, such as at a central station adapted to monitor a plurality of patients, for remote monitoring of the patient by one or more health practitioners. Communication from the pressure transducer 218 to terminal 219' can be effected by wireless transmissions or through cable 220'.

Sometimes, when a urine valve, such as valve 222 in the plumbing arrangement illustrated in FIG. 4, is actuated from a pressure-measurement orientation to a drain orientation, a residual pressure remains in conduit 225 and undesirably is displayed on terminal 219. Therefore, sometimes a zeroing stopcock (not illustrated) may be included in the pressurized fluid path, e.g., such as in a location between three-way fitting 227 and pressure transducer 218.

In the assembly 217 illustrated in FIG. 4, the valve 222 is a remote-actuated valve operated by hydraulic pressure generated by an infusion pump. The infusion pump generates pressure that is used to move a valve member in valve 222 from a drain position, in which the contents of the patient's bladder drain, to a blocking position, in which saline, or other fluid, can be infused into the patient's bladder.

Of course, alternative remote actuation mechanisms are within contemplation in the instant invention, nonexclusively including electrically actuated valves. In one electrically actuated valve within consideration, operation of the infusion pump may be slaved to an electro-mechanical urine valve.

In general, urine valves operable in the present invention may be actuated by human action, hydraulically, or electromechanically. Infusion pumps may similarly be actuated. The entire IAP procedure lends itself to automation to remove a tedious, error prone, burden from health practitioners. With reference to FIG. 4, the pumping system including syringe 212' can be replaced by an automated infusion pump 230. The infusion pump 230 and urine valve 222 can be placed under the control of a control device 231, which can be programmable. Control device 231 can be arranged to communicate with pump 230 (and automated valve 222 in certain cases), using wireless transmissions or wires 232. The collected IAP data is then displayed at convenient locations, such as one or more of terminals 219 and 219'.

The plumbing arrangement illustrated in FIG. 4 can undesirably indicate a "false" pressure, e.g., during the interval when a hydraulically operated remote-actuated valve 222 is actuated between a draining configuration and a bladder infusion or IAP measurement configuration. At such time, the pressure required to actuate the valve 222 is displayed on terminal(s) 219, 219', which does not truly reflect the IAP of the patient. To reduce potential for confusion, it currently is preferred to arrange the transducer 218 in a plumbing arrangement more conducive to indicate only the pressure in the patient's bladder. One such arrangement is illustrated in FIG. 5.

Figure 5:
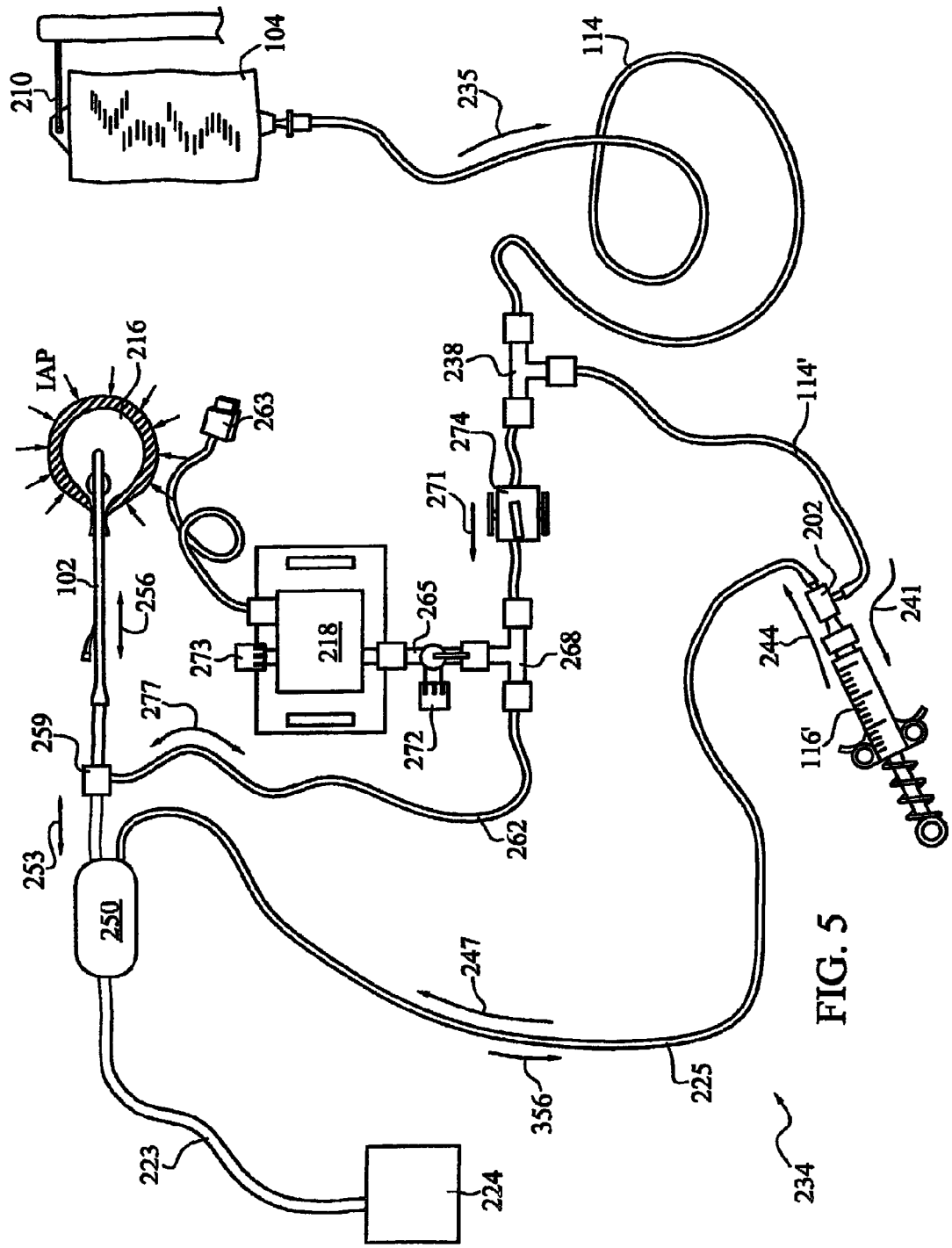
FIG. 5 is a schematic plan view illustrating a fourth and currently preferred arrangement of equipment for measuring a patient's bladder pressure according to principles of the invention.

FIG. 5 illustrates a currently preferred plumbing arrangement, generally indicated at 234, operable to connect devices effective to measure the IAP of a patient. The fluid source may be a saline container 104, as illustrated. In certain arrangements, the saline bag 104 desirably is disposed at an elevation on stand 210, and/or placed into a pressurizable container to generate a "head" pressure in the bag 104. One operable air-activated pressurizable container, generally known as a pressure infuser, is commercially available from the David Clark Company of Worcester, Mass., under the part number 18565G-02, uses an applied air pressure to cause a head pressure in a saline bag 104.

Fluid supply tubing 114 transports saline from the bag 104 under action of a cyclic pump, such as by way of operation of syringe 116'. As illustrated, supply tubing 114 forms a fluid path, indicated by arrow 235, between the bag 104 and a 'T'-fitting 238. Fluid supply tubing 114' continues a fluid path, indicated by arrow 241 toward a flow control device 202. Fluid transported along flow path 241 loads into the syringe as the plunger is retracted. When the syringe's plunger is depressed, loaded fluid flows through fluid supply tubing 225, as indicated by arrows 244 and 247, and into the urine valve 250. A urine valve 250 may be actuated between draining and occluding configurations by direct manual manipulation, or by remote actuation.

In certain embodiments of the invention, it is preferred to use some sort of hydraulically actuated valve as a urine valve 250 to provide a capability for remote actuation of the valve. Energy imparted by the cyclic pump is used to actuate such valve from a draining configuration to an infusion configuration. A plurality of flow control devices are operable as fluid control device 202, as will be discussed further below, depending upon hydraulic requirements of the particular valves 250 employed in the fluid circuit. Similarly, various types of syringes are operable as cyclic pump elements. A choice for a particular type of syringe, for example, spring-assisted such as syringe 116', or hand-operated such as syringe 212, may also be determined by hydraulic requirements of the valve 250 or of other components in the assembly.

In general, once a hydraulic valve 250 is actuated from a draining to an infusion configuration, an additional flow of fluid along path 247 will continue along the flow path indicated by arrows 253 and 256, and into the patient's bladder 216. Once a sufficient bolus of fluid is infused into bladder 216, operation of the fluid pump is stopped, and the pressure of the fluid in the patient's bladder may be measured to infer his/her IAP.

The plumbing arrangement illustrated in FIG. 5 is configured in an effort to indicate the true bladder pressure in the patient at all times. Desirably, a connection 259, effective to place pressure conduit 262 into fluid communication with fluid in path 256, is disposed in-circuit between the bladder 216 and the obstruction in path 253 provided by valve 250. In such an arrangement, pressure generated by the pump and required to actuate the valve 250 is not communicated to pressure transducer 218. Illustrated pressure transducer 218 includes a plug 263 for connection to a monitor, terminal, or other data collection device(s) for display and/or recording of pressure readings.

While connection structure 259 is illustrated as a separate component, such structure 259 may be associated with a valve 250. Furthermore, connector 259 may be configured to assist in maintaining a streamlined, more parallel, arrangement of fluid conduits in the patient's groin area. Similarly, fluid supply tube may be associated with a valve 250 to assist in parallel routing of conduits. For example, fluid supply conduit 225 may be connected to structure at the distal end of valve 250, rather than as illustrated being connected to the proximal end. It is within contemplation for connection structure 259 to encompass alternative conduit structure including a Luer-activated connection at a sampling port of a conduit structured for engagement at a discharge end of the catheter 102. One such alternative conduit structure is commercially available as a component of a urinary drainage bag system available from Bard Medical, a subsidiary of CR Bard, Inc., under the part number 154002.

In the preferred arrangement 234 illustrated in FIG. 5, pressure transducer 218 is in fluid communication with pressure conduit 262 through stopcock 265 and 'T'-fitting 268. It should be realized that the presence of stopcock 265 and 'T'-fitting 268 is not essential. Pressure conduit 262 could be connected to stopcock 265 or directly to pressure transduce 218. In an alternative operable configuration, the positions of transducer 218 and stopcock 265 could be reversed. However, stopcock 265 and 'T'-fitting 268 promote ease of assembly and priming or flushing, and provide additional hydraulic control options. 'T'-fitting 268 allows fluid to flow along the path indicated by arrow 271 from 'T'-fitting 238. Such fluid flow along path 271 can be used conveniently to flush air and bubbles from a fluid path including the pressure conduit 262 and pressure transducer 218. Cover caps 272, 273 can be closed subsequent to purging air from the system.

Preferably, a fluid-flow restriction device 274 is disposed in path 271. Flow restriction device 274 is effective to isolate pressure transducer 218 from any head pressure (psig) associated with the fluid source 104. An operable flow restriction device includes an available valve commercially known as a Delta-Flow, which can be obtained from Utah Medical under part No. 100-204 at internet address http://www.utahmed.com. Such device has a minimum normal flow rate of about 3 ml/hr. At the low flow rate normally permitted by device 274, any fluid flowing along path 271 will be accommodated by expansion of the bladder 216, and therefore will not impact on a pressure indicated by transducer 218.

Typically, the diameter of the catheter 102 is larger than the diameter of conduit 262. A human bladder 216 can change its size rapidly to accommodate a significant volume change under a relatively low increase in pressure. Desirably, conduit 262 is placed into fluid communication with flow path 256 in close proximity to the bladder 216. Therefore, catheter 102 and bladder 216 form a system providing a lower impedance to fluid flow than conduit 262. A flow of drip-infused fluid is accommodated by expansion of the bladder substantially to isolate pressure transducer 218 from such drip-infusion fluid flow. However, fluid flow through a primed conduit 262, responsive to pressure changes in the bladder, is substantially insignificant, so pressure changes in the bladder are indicated by pressure transducer 218 in substantially real time.

Desirably, device 274 can be actuated from its normal configuration to permit a more rapid fluid flow along path 271 to facilitate flushing air from the downstream conduits and components. Illustrated device 274 can be squeezed to actuate it and change its flow characteristics to permit a more rapid, flushing fluid flow. Once the pressure transducer 218 and pressure conduit 262 are flushed, a column of fluid remains, providing 2-way communication, along a path indicated by arrow 277, with fluid in flow path 256. A low flow rate (drip-infusion) in a direction through conduit 262 toward connector 259 is desirable to resist migration of urine or contaminated fluids along path 277 toward pressure transducer 218 during extended periods of use of an IAP assembly.

Figure 6:
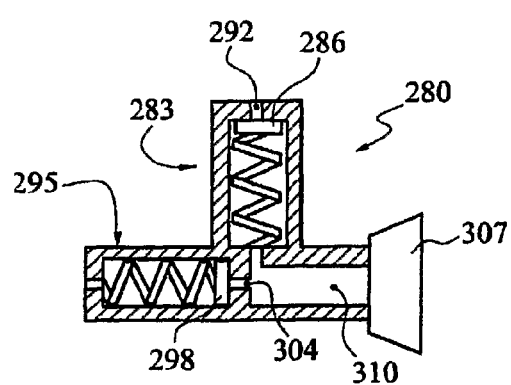
FIG. 6 is a side view, partially in section, illustrating a double check valve.

FIGS. 6 through 9 illustrate three types of valves that are operable for use as an automatic flow-control device 202 (see, FIGS. 2-5). FIG. 6 illustrates a double check valve, generally indicated at 280. One check valve portion, generally indicated at 283, is formed by a sealing element 286 normally biased into engagement with an inlet opening or port 292. A second check valve portion, generally indicated at 295, is formed by sealing element 298 normally biased into engagement with exit port or opening 304. A pressure-cycling pump device, such as a syringe, may be connected in fluid communication with exit port 304 at a third port or conduit through connector 307. The syringe cyclically effects the fluid pressure at a staging area 310 and thereby automatically operates the check valve portions 283 and 295 in correspondence with the high or low pressure generated by the syringe.

Of course, a fluid circuit assembly equivalent to a fluid flow-control device, such as double check valve 280, can be formed by a pair of single check valves and a syringe 116 (or other cyclic-pressure pump) disposed between the two individual check valves. In certain embodiments, a single check valve may be included in a pressure measuring apparatus 200. In one such embodiment, the discrete check valve is located in the fluid path between a fluid source and a syringe 116 to enable multiple syringe discharges without requiring manual valve adjustments to reload the syringe with fluid.

Figure 7:
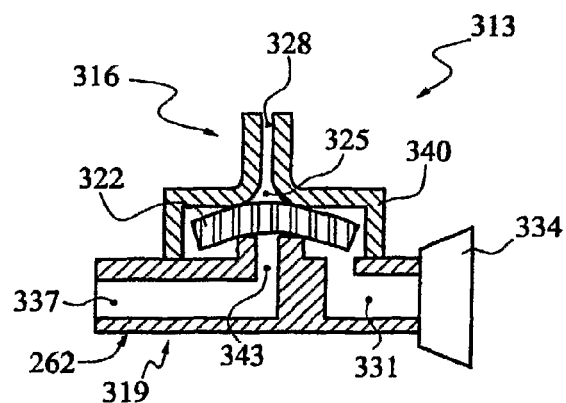
FIG. 7 is a side view, partially in section, illustrating a check-bypass valve operable as a double check valve in the invention.
Figure 8:
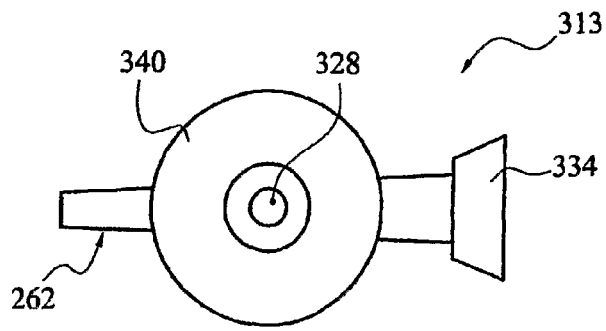
FIG. 8 is a top view of the valve of FIG. 7.

FIGS. 7 and 8 illustrate an embodiment of a check-bypass valve, generally indicated at 313, configured for use in the instant invention. Valve 313 includes a check valve portion, generally indicated at 316, and a bypass valve portion, generally indicated at 319. Check valve portion 316 is formed by resilient member 322 biased into normally sealed engagement over orifice 325. In operation of check valve 316, fluid flows into supply port 328, and past resilient member 322, to a staging area 331. In accordance with one definition of a check valve, fluid flow in the reverse direction would cause seal member 322 to seal tighter over orifice 325, thereby further resisting the flow.

Typically, staging area 331 is in fluid communication with a syringe, such as syringe 116' illustrated in FIG. 2. A cyclic pump may alternatively be employed to vary the pressure in the staging area 331 to operate the valve 313. A syringe may be attached directly to connection structure 334, or may be spaced apart from the valve 313 by use of structure such as a length of tubing.

It is currently preferred for connection structure 334, 307 to be structured as a LUER-LOK™ type fitting, and for structure surrounding inlet port 328 and discharge port 337 to accommodate attachment of tubing by way of a press-on fit. However connection structure 334 may be structured as any other operable connecting structure, including barbs configured for press-fit reception in, or over, a conduit. Likewise, any portion of a valve 313 (or a valve 280, or any other component), that is adapted for connection to a fluid conduit or other device may be structured to form a press-together fit, or to incorporate a portion of a LUER-LOK™ type joint, or a threaded connection, or as any joint providing fluid through-flow and structured to resist fluid leaks.

The illustrated bypass valve portion 319 can operate substantially as a check valve. However, under certain conditions, fluid can flow in either direction between port 337 and staging area 331. In use with the instant invention, pressurized fluid in the staging are 331 causes resilient seal member 322 to deflect into the orifice 325 of housing 340, thereby opening a flow path from staging area 331 though exit port 343 and out of discharge port 337. Contrary to a true check valve, increased fluid pressure at exit port 343 tends to open the flow path by lifting seal member 322 from engagement over exit port 343. Therefore, in certain situations, fluid could flow from discharge port 337 and into staging area 331. In that event, the fluid presumably could be refilling a syringe.

Bypass valve portion 319 is normally closed. Resilient member 322 is biased into sealing engagement over exit port 343 during assembly of the valve 313. Therefore, valve 319 operates as a check valve, to permit fluid flow in only one direction, until fluid pressure at exit port 343 builds to a value operable to overcome the bias in member 322. For low back-pressure applications, such as occurs in making an IAP measurement, bypass valve portion 319 acts as a check valve.

Figure 9:
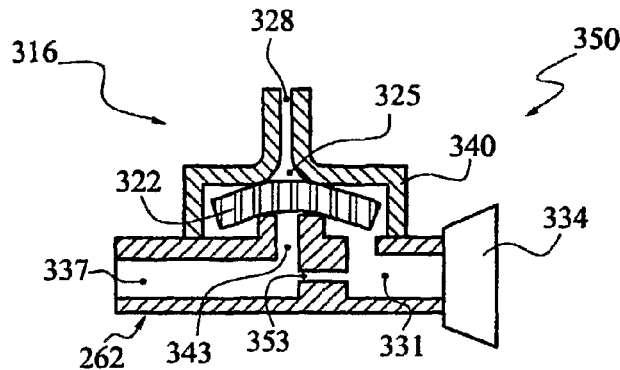
FIG. 9 is a side view, partially in section, illustrating a check/restricted-flow-bypass valve operable as a double check valve in certain embodiments of the invention.

FIG. 9 illustrates a check-bypass/restricted flow valve, generally indicated at 350. Valve 350 is structured much the same as valve 313, but also includes an additional port 353 to provide a fluid path effective to permit a low flow rate between discharge port 337 and staging area 331. Such an arrangement permits a certain amount of fluid to be removed from a remotely-actuated hydraulically operated valve, effective to assist in returning that valve to a drain configuration. Flow through conduit 225 of such removed fluid is indicated by arrow 356 in FIG. 5.

Currently, it is desired to include a check-bypass/restricted flow valve 350 in plumbing arrangements including a remotely actuatable valve 204 that is hydraulically actuated in both directions, between a drain configuration and an infusion configuration. However, it is within contemplation that certain remotely actuatable valves 250 can operate as an equivalent to a check valve component of valve 202. In such case, a simple check valve could be installed in place of valve 202 illustrated in FIG. 5. The replacement check valve would be installed in-circuit to permit flow from the fluid source 104 in a direction toward the cyclic pump.

FIGS. 10 through 13 illustrate certain functional details of an operable remotely actuatable hydraulic urine valve, generally indicated at 360. Valve 360 includes a piston 362 carried inside housing 364. Piston 362 includes piston sleeve 366 carrying an affixed end cap 368. Resilient element 370 (if present) is conveniently trapped by assembly of cap 368 and sleeve 366 effective to bias piston 362 away from an infusion configuration (illustrated in FIG. 11) and toward a draining configuration (illustrated in FIG. 10). At a draining configuration, urine, or other fluids, entering drain entrance port 372 may freely flow through valve 360 and out of drain exit port 374. Housing cap 376 is typically permanently affixed to housing 364 after the piston 362 is installed in housing 364.

As indicated in the preceding paragraph, resilient element 370 is not required for operation of a remotely actuatable hydraulic urine valve 360. In certain instances, a resilient element may be provided operable to urge piston 362 only a portion of the distance between an infusion configuration and a draining configuration. In other embodiments of a valve 360, a resilient element 370 may be provided that is operable to urge displacement of piston 362 over the entire distance from an infusion configuration to a draining configuration. Resilient element 370 may be a spring, as illustrated, or some other compressible component, such as a section of elastic tubing. In an alternative construction, it is within contemplation for a resilient element 370 to be disposed to act between distal face 377 of piston 362 and housing cap 376.

The interior of housing 364 may be regarded as defining a drain subchamber 378 and an infusion subchamber 380 that are separated by piston 362 and sliding seal element 381. Desirably, seal element 381 is arranged as a wiping seal operable to assist in maintaining at least reasonable cleanliness in the infusion subchamber 380. During operation of valve 360, fluid entering through infusion port 382 fills and enlarges infusion chamber 380, effective to displace piston 362 distally toward cap 376. Eventually, piston 362 is displaced sufficiently to engage seal surface 384 and seal element 386 (e.g., an O-ring) carried by cap 376. At that position, a fluid flow path through conduit 372 toward drain exit port 374 is occluded.

It should be understood that FIGS. 10-14 are illustrative of the working principles of one embodiment of a hydraulically actuated valve 360. Such illustrations are simplified, to increase clarity of certain illustrated structure, and to promote clarity of a description of operation of the valve. For example, structure encompassed in certain ports, such as infusion port 382, drain entrance port 372, and drain exit port 374, and not illustrated, may include connection structure adapted to interface with conduit structure, or other components of the LAP system.

Figure 11:
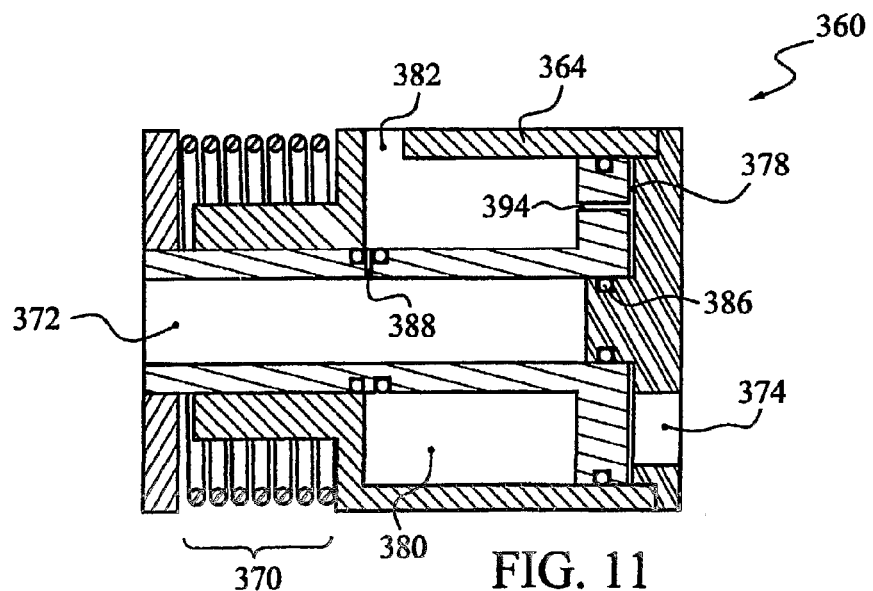
FIG. 11 is a cross-section view in elevation through a plane passing through a centerline of the urine valve illustrated in FIG. 10, with the valve shown in bladder filling configuration.
Figure 12:
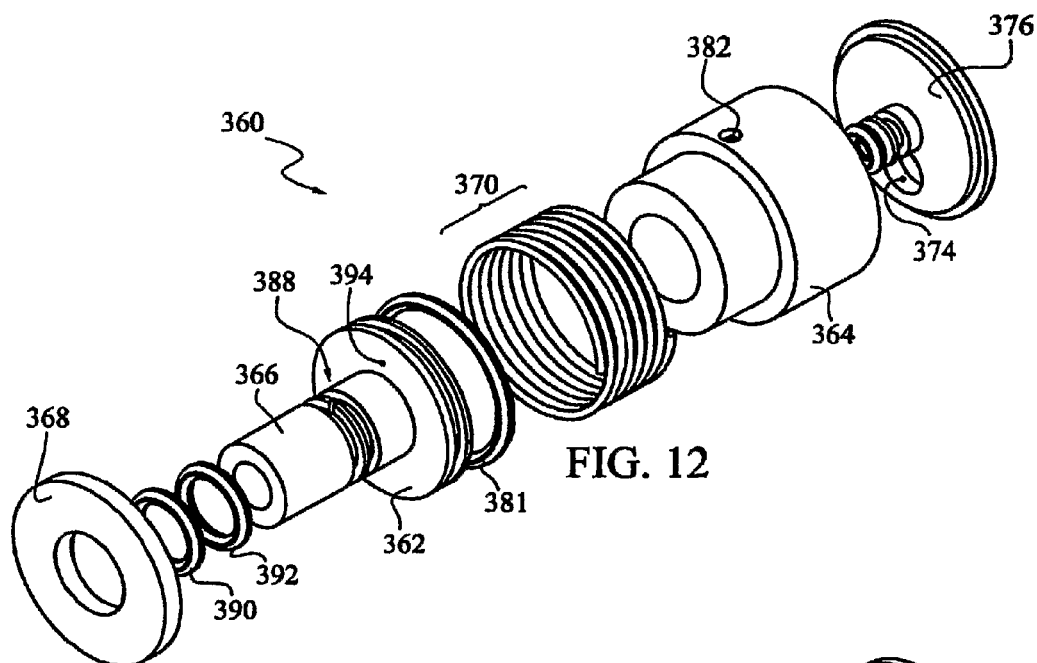
FIG. 12 is a exploded assembly view in perspective from a proximal end of the urine valve illustrated in FIG. 10.
Figure 13:
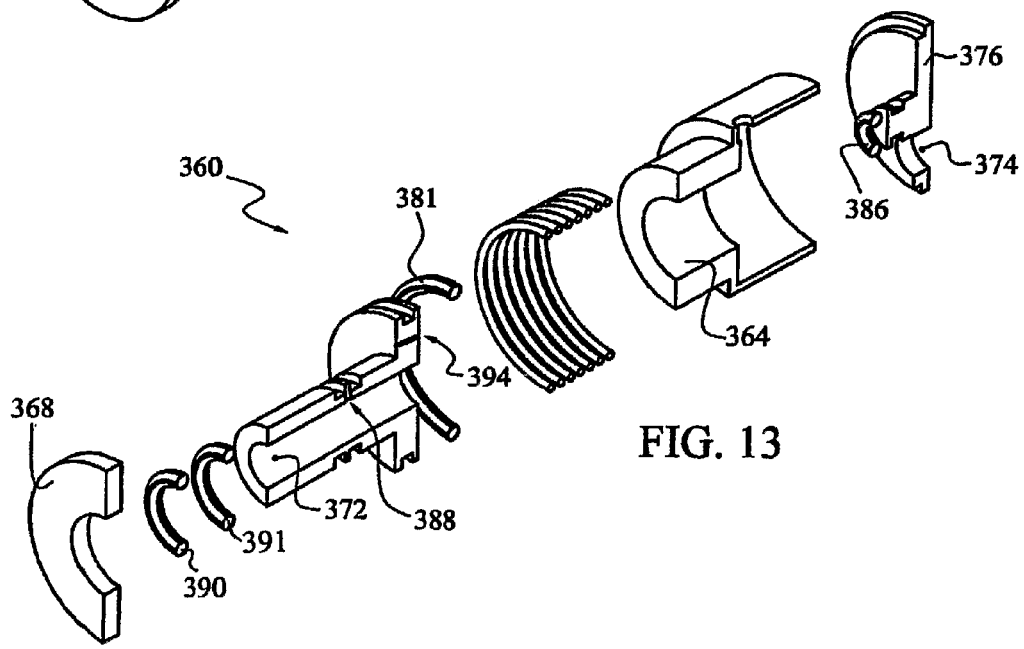
FIG. 13 is a sectional exploded assembly view in perspective of the urine valve illustrated in FIG. 10.
Figure 14:
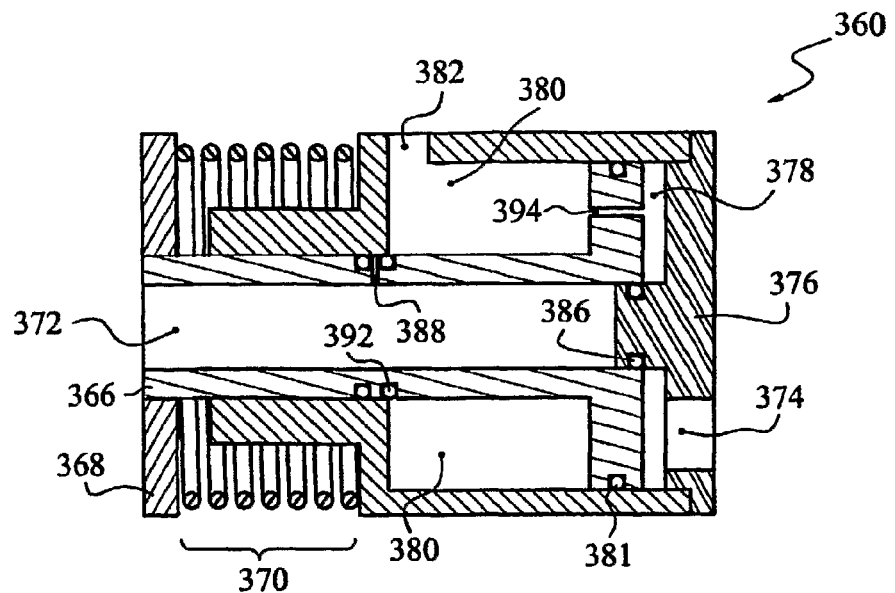
FIG. 14 is a cross-section view in elevation through a plane passing through a centerline of the urine valve illustrated in FIG. 10, with the valve shown in bladder pressure measuring configuration.

Typically, piston 362 must be displaced by an additional amount, beyond the point of first drain occlusion, to place bypass port 388 into fluid communication with infusion subchamber 380. Such configuration is referred to as an infusion configuration, and is illustrated in FIG. 11. When valve 360 is placed into the infusion configuration, additional fluid passing through infusion port 382 will be directed through drain entrance port 372 and toward a patient's bladder 216 along flow path 253 (see FIG. 5). One or more bypass port 388 may be provided spaced apart around a circumference of piston sleeve 366.

Desirably, valve 360 is configured to occlude a flow path through bypass port 388, substantially automatically, when an infusing fluid flow through infusion port 382 terminates. Such occlusion resists a back-wash fluid flow into the infusion subchamber to reduce chance of contamination in a fluid supply conduit 225. One operable construction to effect such occlusion of bypass port 388 is best illustrated with reference to FIGS. 11 and 14. First bypass seal 390 and second bypass seal 392 are arranged in harmony with bypass port 388 such that a sufficiently reduced fluid pressure at infusion port 382 permits spring 370 to displace piston 362 operably for a portion of housing 364 to occlude the entrance to bypass port 388. Fluid present in the infusion subchamber 380 simply drains through bypass port 388 as piston 362 displaces under the urging of the resilient member 370. Additional fluid flow from the infusion chamber 380 through bypass port 388 is resisted once the bypass port 388 is occluded by structure of housing 364. A pressure measurement configuration (see FIG. 14) for the valve 360 may be defined as being produced when the piston 362 is disposed between a first occluding position for bypass port 388 and a first opening of the occlusion formed between seal 386 and bore surface 384.

Figure 10:
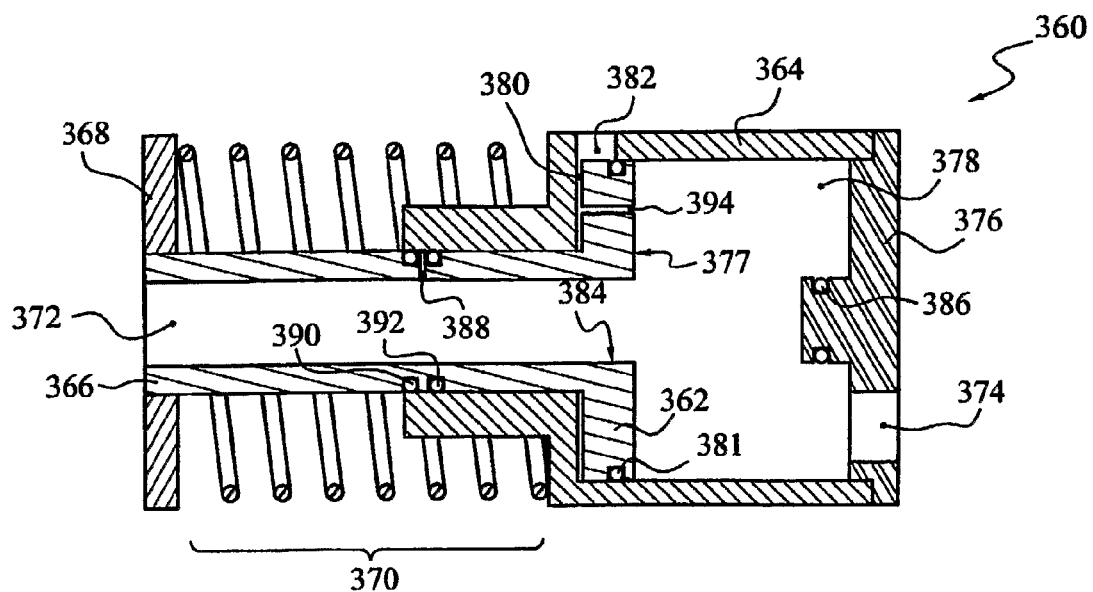
FIG. 10 is a cross-section view in elevation through a plane passing through a centerline of an operable remote-control urine valve, with the valve shown in bladder draining configuration.

A valve 360, structured as described thus far and even without a resilient element 370, would be hydraulically operable between a draining configuration and an infusion configuration. Actuation from draining to infusion configurations, and back again, could be controlled entirely by pressure and fluid flow generated by a pumping device, such as a syringe. Withdrawing sufficient fluid from the infusion subchamber 380 (e.g., along path 356 in FIG. 5) would displace piston 362 toward the left (proximally), as illustrated in FIG. 10, placing the valve 360 into a draining configuration. Such a valve may be characterized as being fully hydraulic.

With reference now to FIG. 5, when valve 250 is a fully hydraulic valve, it is generally desirable to replace illustrated syringe 116' with a syringe structured similarly to syringe 212, illustrated in FIG. 3. The replacement syringe desirably has sufficient capacity to provide the desired bolus of infusion fluid to effect an IAP measurement in a single stroke. The plunger of the loaded syringe is depressed to infuse the patient's bladder, and left in the depressed position until the pressure measurement is made. Then, the plunger is retracted to open the valve 250 and also reload the plunger with the next bolus of infusion fluid.

The amount of fluid to open a fully hydraulic valve 250 desirably is small, perhaps less than about 3 ml, so flow indicated by arrow 356 is small. A single check valve may be used to form a portion of a flow device 202, to permit the syringe to extract fluid from the valve 250. Once valve 250 is fully opened, it can act as a check valve component of an equivalent flow control device 202. Alternatively, a check-bypass/restricted flow valve, such as valve 350, may be used as a flow control device 202.

Referring again to FIGS. 10-14, it is sometimes desirable to provide a remotely actuatable valve 360 with a substantially autonomic closing capability. By autonomic closing capability, it is meant that a valve element would be displaced from an infusion configuration to a draining configuration without requiring further user input. However, in an apparatus arranged to infer a patient's IAP, it is desirable also to provide a time interval during which the valve remains occluded to permit a pressure measurement to be made prior to placing the valve into draining configuration.

One structural arrangement operable to effect such a time-delayed autonomic closing is included in illustrated valve 360. The autonomic time-delay structure includes bleed-down port 394. Bleed-down port 394 is sized to provide a restricted fluid-flow path between infusion subchamber 380 and drain subchamber 378. A diameter of port 394 may be sized in harmony with a volume of fluid trapped in subchamber 380, and with a displacing force provided by resilient element 370, such that a desired time interval transpires as piston 362 is slowly displaced from a fluid trapping position to a draining configuration. A desirable time interval, in which to effect a pressure measurement to infer IAP, is currently believed to be about 20-30 seconds.

It currently is currently preferred for a urine valve to maintain a "smooth" or "blunt" contact area, at a potential patient interface, when actuated to either pressure measurement or fluid draining configurations. Also, indicator structures, if present, desirably have a relatively low profile to avoid inflicting patient discomfort if brought into contact with the patient's leg.

Certain remotely actuated valves benefit from the presence of indicia to show the current flow path through the valve. Such indicia may assist in diagnosing possible causes of unexpected pressure readings. In rotationally-activated hydraulic valve 222 (see, FIGS. 3, 4) an indicator 466 is placed into axial agreement with alignment indicator 468 when valve 222 is oriented in a drain configuration. Indicators 466, 468 may protrude slightly from a surface of housings portions of valve 222 to provide both tactile and visual feedback to a valve operator. Such indicators are only one example able to provide visual feedback for a health practitioner to verify return of a urine valve to a drain configuration.

It is within contemplation to form a piston 362, or other element operable as a valve gate, that is visible (e.g., through a transparent housing 364 (see, FIGS. 10-13)) to alternatively, or additionally, indicate a valve flow path setting. It is further within contemplation to provide written indicia to spell out a flow path corresponding to a particular valve orientation. It is also within contemplation to provide remote a manual override effective to manually fix a "stuck" valve.

Figure 15:
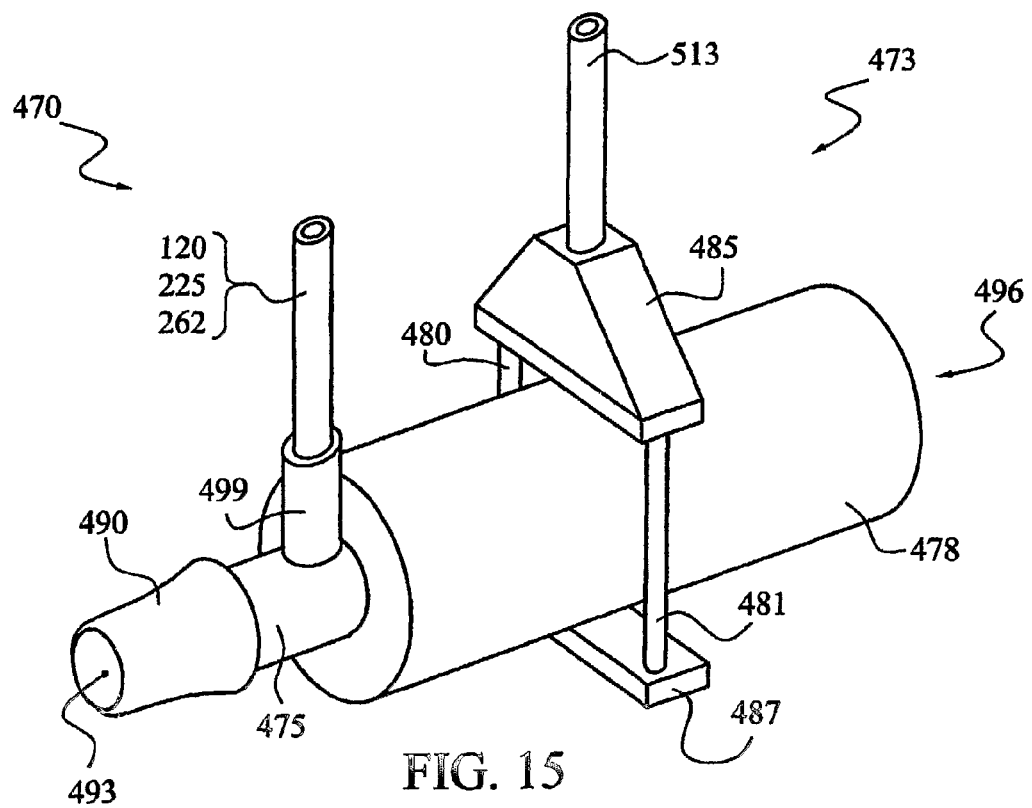
FIG. 15 is a view-in perspective of an alternative valve arrangement effective to occlude a urine drain conduit under control of an operator located remote from the drain conduit.
Figure 16:
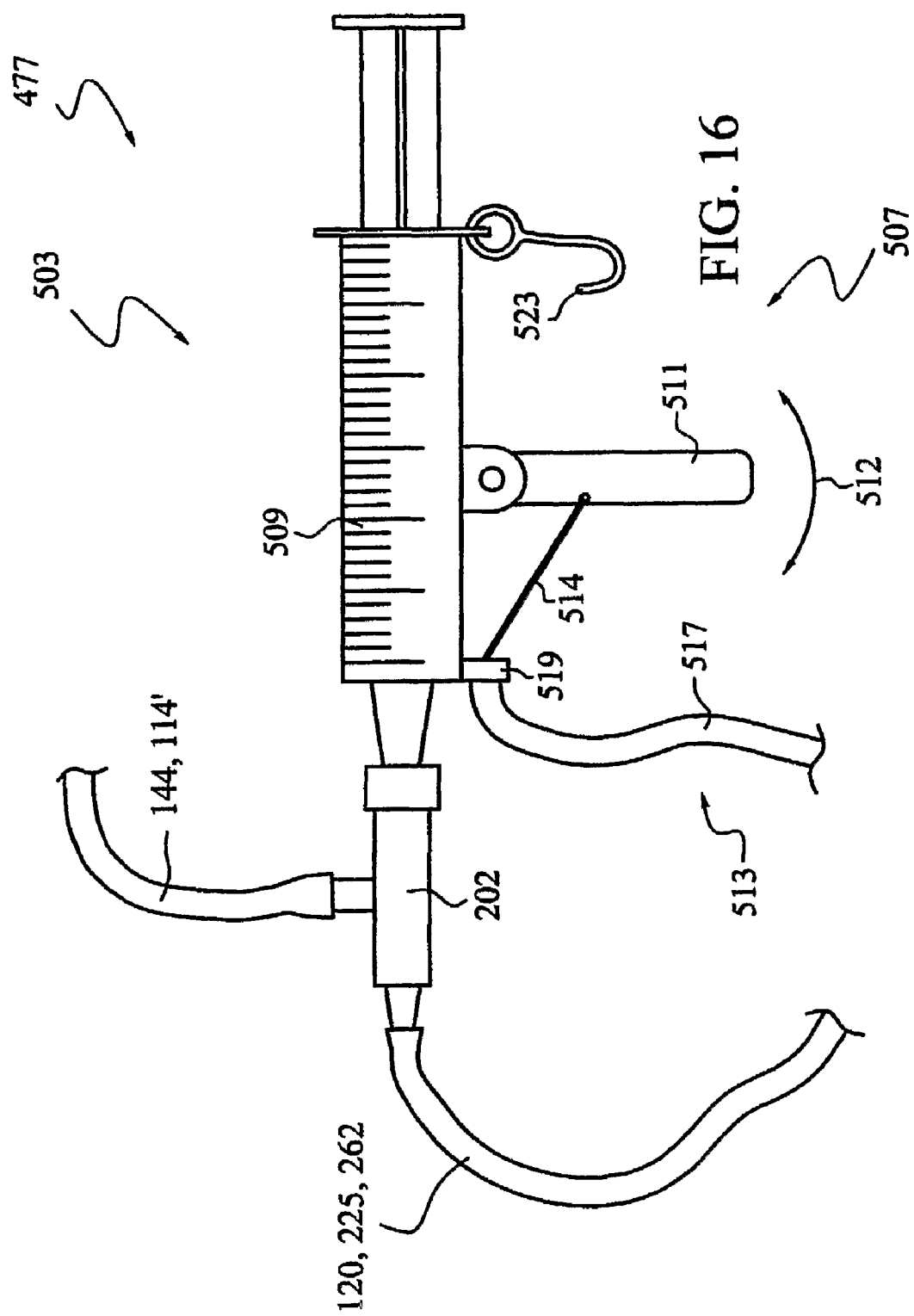
FIG. 16 is a view-in perspective of one conveniently arranged dual-purpose remote-control device operable to actuate the valve of FIG. 15, and also to infuse fluid into a patient's bladder.

FIGS. 15 and 16 illustrate an alternative assembly 470 effective to permit occlusion of a urine drain path and infusion of fluids into a patient's bladder under control of personnel located at a convenient and remote location. Assembly 470 includes a remotely actuated valve generally indicated at 473, coupling conduit 475, and an actuator assembly generally indicated at 477. Assembly 470 may be installed in-circuit as illustrated in any of FIGS. 2-5, in replacement of corresponding structure.

Illustrated valve 473 is a conduit clamp-style valve that may be actuated between draining and occluding configurations mechanically, as illustrated. Such clamp-style valves typically provide simplicity, low cost, and reliability in maintaining a sterile field inside conduit structure during extended use of an IAP apparatus. In certain alternative construction, a clamp-style valve 473 may be operated hydraulically, or by an electro-mechanical device, such as a solenoid driven clamp arrangement. In certain less desirable embodiments of the invention, it is within contemplation to configure a remotely actuated valve 473 as a cable-actuated gate valve.

It is preferred for a valve 473 to be maintained in association with flexible conduit member 478, to ensure reliable operation. Illustrated valve 473 includes a pair of actuating cables 480, 481, effective to maintain valve 473 in position along an axis of conduit 478. Cables 480, 481 are retracted to clamp and occlude tube 478 between top gate member 485 and bottom gate member 487. It is important also to ensure clamp valve 473 remains in position to squeeze a transversely manipulatable portion of the conduit 478 (e.g., a section not reinforced by a portion of conduit connector 475). Sometimes, axial protrusions (not illustrated) are provided to resist axial migration of valve 473 with respect to tube 478. Alternatively, one or more of top gate 485 and bottom gate 487 may be affixed to tubing section 478. Of course, other arrangements (not illustrated), of known clamp-type conduit valves are operable in alternative embodiments of the invention.

With reference to FIG. 15, coupling conduit 475 is adapted at barbed proximal end 490 to engage through-bore 493 in fluid communication with a discharge end of a catheter 102. A fluid-tight connection at proximal end 490 may be made directly with such catheter 102, or may include intermediate conduit structure. One arrangement of intermediate structure is illustrated in FIG. 5, and is operable to place pressure transducer 218 substantially in isolation from pressure spikes associated with pumping of infusion fluids into the bladder 216. Distal connection end 496 of tubing 478 provides coupling structure effective to place through-bore 493 in fluid communication with a drain receptacle, such as bag 224 in FIG. 3. Desirably, coupling conduit 475 includes a connection structure 499, operable to place an infusion conduit (e.g., 120, 225, 262) in fluid communication with through-bore 493.

Connection structure 499 may be configured to receive any desired cooperating connection device, as dictated by the fluid circuit assembly. For example, it is within contemplation for connector 499 to be nonexclusively embodied as a urine collection/aspiration port adapted to receive an infusion needle 122; as a simple 'T' intersection; or as a luer-activated sample port. Connector 499 may also be associated with a check valve to resist migration of fluids discharged from the bladder in an "upstream" direction into an infusion conduit.

FIG. 16 illustrates one workable actuator assembly 477 operable to remotely control valve 473, and also to infuse fluids into a patient's bladder 216. Assembly 477 includes a dual function syringe, generally indicated at 503. Syringe 503 includes a valve actuation assembly, generally indicated at 507, and an integral infusion syringe portion 509. Syringe portion 509 may be structured in accordance with known syringes, including any of the embodiments illustrated in FIGS. 1-5. For convenience, syringe portion 509 and valve actuator portion 507 are integrated as a single assembly. It is within contemplation also to provide each actuator portion as a separate component. However, it is currently believed to be more convenient (e.g., to an anesthesiologist), to combine the control apparatus into a single assembly to reduce clutter in an operatory.

Valve actuation assembly 507 includes a pivoting lever actuator, or handle 511. Handle 511 may conveniently be mounted for pivotal rotation, indicated by arrow 512, with respect to syringe 509 in a working relationship with a control cable, generally indicated at 513. An orientation of handle 511 may provide feedback indicating a configuration of a remotely actuated valve—occluding or draining. Handle 511 is affixed to an end of cable element 514, and control cable sheath 517 abuts holding structure 519. Therefore, rotation of handle 511 is effective to extract or replace a section of cable element 514 from or into cable sheath 517. Cable element 514 operates on cables 480 and 481 to move gate 487. Biasing structure (not illustrated) may be provided to urge gate 487 toward a draining configuration, in the event that a sufficient restoring force is not supplied by tubing 478. Keeper structure, such as illustrated keeper hook 523, may be provided to hold handle 511 in position effective to maintain a remote valve in a drain occluding configuration during a pressure measurement interval. Alternative keeper structures within contemplation nonexclusively include: ratchet assemblies, friction interfaces, and toggle-action mechanisms.

It is currently preferred to injection mold certain valve components in straight-pull, simple molds to reduce mold-making and attendant manufacturing costs. Molded valve components may be formed from a variety of medical grade plastics, including polycarbonate, ABS, acrylic, and polyethylene. Valve seals may be structured other than as the illustrated O-rings, including as self-biased flap structures. O-ring seals may be formed from suitable rubber-like materials, with silicone currently being preferred. A variety of bonding procedures are operable to join valve components to form a valve assembly, including plastic welding techniques such as solvent, ultrasonic, friction, shear, and heat welding, as well as adhesive bonding techniques.

While the invention has been described in particular with reference to certain illustrated embodiments, such is not intended to limit the scope of the invention. The present invention may be embodied in other specific forms without departing from its spirit or essential characteristics. The described embodiments are to be considered as illustrative and not restrictive. For example, one or more component in a particular illustration may be combined with one or more other component in one or more different illustration. The scope of the invention is, therefore, indicated by the appended claims rather than by the foregoing description. All changes which come within the meaning and range of equivalency of the claims are to be embraced within their scope.

What is claimed is:

1. An apparatus for measuring hydraulic pressure in the bladder of a medical patient to infer intra-abdominal pressure in that patient, the apparatus comprising:
   a catheter adapted for draining urine from the bladder;
   a container of infusion fluid;
   a first fluid path providing fluid communication between said container and a drain portion of said catheter;
   a pump disposed to urge fluid flow, under dynamic fluid flow conditions that inherently generate friction loss and consequently require elevated pressure, compared to true bladder pressure, to be induced by the pump to overcome the friction loss, through said first fluid path;
   a pressure transducer disposed in fluid communication with the bladder and sufficiently hydraulically isolated from the pressure induced by said pump effective to generate a signal responsive substantially to true gage pressure of fluid in the bladder during operation of said pump to urge said fluid flow; and
   a urine valve, arranged in-circuit effective at a first configuration to resist a draining discharge from said catheter while a bolus of said infusion fluid is infused into the bladder, and effective at a second configuration to permit a draining discharge from said catheter.

2. The apparatus of claim 1, wherein:
   said pressure transducer is further substantially hydraulically isolated from a head pressure associated with said container of fluid.

3. The apparatus of claim 1, said urine valve being remotely actuatable to change a configuration of said valve from said first configuration to said second configuration, wherein:
   a gate component of said valve is displaced, by a hydraulic input received from said pump, effective to resist said draining discharge.

4. The apparatus of claim 3, wherein:
   a gate component of said valve is displaced, effective to permit said draining discharge, by a hydraulic input received from said pump.

5. The apparatus of claim 3, wherein:
   a gate component of said valve is urged toward an open position, effective to permit said draining discharge, by a biased member of said valve.

6. The apparatus of claim 5, wherein:
   said biased member comprises a resilient element disposed for biasing by action of said hydraulic input.

7. The apparatus of claim 6, further comprising:
   a time-delay mechanism adapted to permit substantially autonomic opening of said valve to effect said draining discharge.

8. The apparatus of claim 3, wherein:
   said urine valve comprises a remote-actuated conduit clamp valve.

9. The apparatus of claim 3, wherein:
   said valve comprises a housing defining a chamber having a volume, with an infusion port and a drain exit port being in fluid communication with said chamber;
   said gate component comprises a piston having a portion disposed to reciprocate between first and second positions in said chamber and operable to divide said chamber into at least a first subchamber and a second subchamber, said infusion port being in fluid communication with said first subchamber, said drain exit port being in fluid communication with said second subchamber, said piston further being associated with a drain entrance port and a bypass port; wherein:
      at said first position, structure of said valve is configured to permit fluid communication between said drain entrance port and said drain exit port while resisting fluid communication between said drain entrance port and said infusion port; and
      at said second position, structure of said valve is configured to permit fluid communication between said drain entrance port and said infusion port by way of said bypass port while resisting fluid communication between said drain entrance port and said drain exit port.

10. The apparatus of claim 9, wherein:
    said piston is biased toward said first position such that said bypass port is occluded by structure associated with said housing substantially upon cessation of flow of said infusion fluid through said infusion port and into said first subchamber.

11. The apparatus of claim 9, further comprising:
    a time-delay mechanism adapted to permit substantially autonomic opening of said valve to effect said draining discharge, said time-delay mechanism comprising:
       a bleed-down port having a cross-section sized to provide restricted fluid flow therethrough between said first subchamber and said second subchamber; and
       a resilient member biased to urge said piston toward said second configuration.

12. A method for measuring hydraulic pressure in the bladder of a medical patient to infer intra-abdominal pressure in that patient, the method comprising:
    a) providing a catheter adapted for draining urine from the bladder, a container of infusion fluid, a pump, a pressure transducer; and a urine valve;
    b) placing said urine valve in-circuit between a drain portion of said catheter and a receptacle;
    c) placing said pump in-circuit between said urine valve and said container;
    d) placing said pressure transducer in-circuit with said catheter effective to substantially hydraulically isolate said pressure transducer from pressure fluctuations associated with actuation of said valve;
    e) bleeding air from the circuit;
    f) placing said urine valve into a draining configuration, for a first period of time, to permit flow between said catheter and said receptacle while resisting flow between said container and said catheter;
    g) placing said urine valve into an infusion configuration, for a second period of time, to resist flow between said catheter and said receptacle while permitting flow between said container and said catheter;
    h) infusing a desired bolus of said infusion fluid into the bladder during said second period of time;
    i) measuring a pressure in the bladder at least once during a third period of time while said urine valve is in a pressure-reading configuration; and j) returning said urine valve to said draining configuration subsequent to lapse of said third period of time.

13. The method of claim 12, wherein step d) further comprises, in any order:
applying a first pressure, above atmospheric pressure, to said infusion fluid; and
placing said pressure transducer in-circuit in a first fluid path effective substantially to isolate said pressure transducer from said first pressure and to permit a low-rate fluid flow in the first fluid path without requiring fluid flow in a second fluid path extending to the pump.

14. The method of claim 12, wherein during step g):
operating said pump for a portion of said second period of time is effective to cause a gate member of said urine valve to displace operably to place said urine valve into said infusion configuration.

15. The method of claim 14, wherein during step j):
operating said pump is effective to cause a gate member of said urine valve to displace operably to return said urine valve to said draining configuration.

16. The method of claim 14, wherein during step j):
a gate member of said urine valve is configured and arranged in harmony with a time-delay mechanism effective to maintain said urine valve in said pressure-measuring configuration during said third period of time and then effective autonomically to return said urine valve to said draining configuration.

17. The method of claim 12, further comprising, prior to step e):
applying a pressure above atmospheric pressure to said infusion fluid.

18. The method of claim 13, wherein step e) comprises:
actuating a flow restriction device disposed in-circuit between said container and said pressure transducer operably to permit an increased flow rate through said flow restriction device.

19. An apparatus for measuring hydraulic pressure through a catheter adapted to drain urine from the bladder of a medical patient to infer intra-abdominal pressure in that patient, the apparatus comprising:
structure defining a first fluid path to provide fluid communication between a container of infusion fluid and a drain end of said catheter;
a pump disposed to urge fluid flow through said first fluid path;
structure adapted to place a pressure transducer in fluid communication with fluid downstream of said pump; and
a urine valve, arranged in-circuit effective at a first configuration to resist a draining discharge from said catheter while a bolus of infusion fluid is infused into the bladder, and effective at a second configuration to permit a draining discharge from said catheter, said urine valve comprising a time-delay mechanism adapted to permit said urine valve to resist said draining discharge for a first period of time comprising at least about 20 seconds subsequent to termination of a valve-closing command input and, subsequent to expiration of said first period of time, to autonomically return to said second configuration.

20. The apparatus according to claim 19, wherein:
said time-delay mechanism comprises:
a biased seal member displaceable beyond a first-sealed position to entrap a volume of timing fluid, said first-sealed position occluding a drain path from said catheter; and
a bleed-down aperture sized to provide restricted fluid flow there-through and arranged in an escape path for said timing fluid, said timing fluid being urged toward said bleed-down aperture by said biased seal member.

* * * * *